(12) United States Patent
Carmel

(10) Patent No.: US 10,512,956 B2
(45) Date of Patent: Dec. 24, 2019

(54) SYSTEM AND METHODS FOR CONVERSION OF BIOHAZARD TO MUNICIPAL WASTE

(71) Applicant: CELITRON MEDICAL TECHNOLOGIES KFT, Vác (HU)

(72) Inventor: Itzhak Carmel, Mevaseret Tzion (IL)

(73) Assignee: CELITRON MEDICAL TECHNOLOGIES KFT, Vac (HU)

( * ) Notice: Subject to any disclaimer, the term of this patent is extended or adjusted under 35 U.S.C. 154(b) by 725 days.

(21) Appl. No.: 15/169,041

(22) Filed: May 31, 2016

(65) Prior Publication Data

US 2016/0346817 A1    Dec. 1, 2016

Related U.S. Application Data

(62) Division of application No. 13/885,749, filed as application No. PCT/IL2011/000775 on Oct. 4, 2011, now abandoned.

(Continued)

(51) Int. Cl.
*B09B 3/00*    (2006.01)
*A61L 2/07*    (2006.01)
(Continued)

(52) U.S. Cl.
CPC ............ *B09B 3/0075* (2013.01); *A61L 2/07* (2013.01); *A61L 11/00* (2013.01);
(Continued)

(58) Field of Classification Search
CPC ... B02C 19/0075; B02C 19/186; B02C 23/16; B02C 23/18; B02C 23/24; B09B 3/0075; A61L 11/00; A61L 2/07
(Continued)

(56) References Cited

U.S. PATENT DOCUMENTS 326,853 A * 9/1885 Cormack ................. B02C 9/02
241/274
1,921,914 A * 8/1933 Edman ................ B02C 13/1814
241/14
(Continued)

FOREIGN PATENT DOCUMENTS

CN    2128173 Y    3/1993
CN    1130355 A    9/1996
(Continued)

OTHER PUBLICATIONS

"We Think Green, Integrated Sterilizer & Shredder (ISS)" Unique Technology, Cation. Medical Technologies. Sep. 2010.

*Primary Examiner* — Faye Francis
(74) *Attorney, Agent, or Firm* — Browdy and Neimark, P.L.L.C.

(57) ABSTRACT

A system for shredding medical waste, the system comprising a medical waste treating chamber being an interior of an enclosure disposed within an environment which is not to be polluted, a motor, a shredder seated in the chamber and including a motor-driven shaft and blades rotated by the shaft, the shaft extending through the enclosure thereby to define an interface between the waste treating chamber and the environment, and interface seal apparatus preventing leakage of at least fluids from the medical waste treating chamber into the environment, via the interface.

21 Claims, 37 Drawing Sheets

Related U.S. Application Data

(60) Provisional application No. 61/414,071, filed on Nov. 16, 2010.

(51) Int. Cl.
  *A61L 11/00* (2006.01)
  *B02C 19/00* (2006.01)
  *B02C 19/18* (2006.01)
  *B02C 23/16* (2006.01)
  *B02C 23/40* (2006.01)
  *B02C 18/00* (2006.01)
  *B02C 18/08* (2006.01)
  *B02C 18/16* (2006.01)

(52) U.S. Cl.
  CPC .......... *B02C 18/0084* (2013.01); *B02C 18/08* (2013.01); *B02C 18/16* (2013.01); *B02C 19/0075* (2013.01); *B02C 19/186* (2013.01); *B02C 23/16* (2013.01); *B02C 23/40* (2013.01); *B09B 3/0091* (2013.01); *A61L 2202/11* (2013.01); *A61L 2202/17* (2013.01); *B02C 2018/164* (2013.01)

(58) Field of Classification Search
  USPC ...................... 241/166, 167, 73.95
  See application file for complete search history.

(56) References Cited

U.S. PATENT DOCUMENTS

| | | | |
|---|---|---|---|
| 2,226,317 A * | 12/1940 | Myers | B02C 18/34 |
| | | | 15/104.001 |
| 3,528,617 A * | 9/1970 | Trevathan | B02C 18/08 |
| | | | 241/167 |
| 4,637,557 A * | 1/1987 | Vitunac | B02C 13/284 |
| | | | 209/384 |
| 5,078,924 A | 1/1992 | Spinello | |
| 5,163,375 A | 11/1992 | Withers et al. | |
| 5,236,135 A | 8/1993 | Wilson et al. | |
| 5,240,187 A | 8/1993 | Wilson | |
| 5,271,892 A | 12/1993 | Hanson et al. | |
| 5,348,235 A | 9/1994 | Pappas | |
| 5,362,443 A | 11/1994 | Tanaka et al. | |
| 5,379,951 A * | 1/1995 | Hughes | B02C 18/067 |
| | | | 241/101.761 |
| 5,383,613 A * | 1/1995 | Sundquist | A47J 43/0705 |
| | | | 241/166 |
| 5,387,350 A | 2/1995 | Mason | |
| 5,401,444 A | 3/1995 | Spinello | |
| 5,424,033 A | 6/1995 | Roland | |
| 5,458,072 A | 10/1995 | Hughes et al. | |
| 5,508,004 A | 4/1996 | Held et al. | |
| 5,580,521 A | 12/1996 | Gagne | |
| 5,639,031 A | 6/1997 | Wright et al. | |
| 5,800,776 A | 9/1998 | Morgantini et al. | |
| 5,830,419 A | 11/1998 | Held et al. | |
| 5,833,922 A | 11/1998 | Held et al. | |
| RE36,486 E * | 1/2000 | Hughes | B02C 18/067 |
| | | | 241/101.761 |
| 6,039,724 A | 3/2000 | Seifert et al. | |
| 6,113,854 A | 9/2000 | Milum et al. | |
| 6,194,564 B1 * | 2/2001 | Murofushi | C08B 37/0033 |
| | | | 210/174 |
| 6,818,178 B2 | 11/2004 | Kohl et al. | |
| 7,144,550 B2 | 12/2006 | Devine et al. | |
| 7,718,120 B2 | 5/2010 | Paskalov | |
| 7,814,851 B2 | 10/2010 | Tashiro | |
| 7,815,851 B1 | 10/2010 | Lewis | |
| 9,265,846 B2 | 2/2016 | Bala | |
| 2003/0145806 A1 | 8/2003 | Tokutake et al. | |
| 2011/0083566 A1* | 4/2011 | Backus | A47J 19/027 |
| | | | 99/511 |

FOREIGN PATENT DOCUMENTS

| | | |
|---|---|---|
| CN | 200951435 Y | 9/2007 |
| EP | 1520592 A1 | 4/2005 |
| JP | 2008054841 A | 3/2008 |

* cited by examiner

FIG. 2A

Step 15: Loading: waste is loaded into the chamber 4, chamber's door closes. Then, chamber rotates to process position e.g. fully vertical as shown in Fig. 1c.

Step 20: Shredding: The shredder 2 starts its operation, typically at different speeds, as appropriate to the application. For example, the shredder may initially operate back/forward at high speed, e.g. 3 seconds forward, 3 seconds backward, for 3 minutes, and then subsequently may operate 30 seconds forward, 30 seconds backward, again at high speed till exhaust stage (step 50 in Fig. 2b).

Step 30: Prevacuum: The cycle starts with one vacuum pulse to 35kPa, to remove the air from the chamber 4.

Step 40: Heating : Steam is introduced into the chamber until sterilization temperature is reached, e.g. 134°C and pressure of 312kPa. temperature and pressure are controlled at a suitable sterilization level for the duration of sterilization. A Bio Filter valve (e.g. VI in Fig. 11a) typically operates in shoot mode e.g. 3 seconds opened and 30 seconds closed, throughout the sterilization stage.

To Fig. 2b, step 45

FIG. 2B

From Fig. 2a, step 40

↓

Step 45 : Sterilization: Temperature and pressure are maintained at a suitable level, e.g. 134°+4° and 312kPa+28kPa, for 5 minutes.

Cycle fail: If during the sterilization process, the cycle fails, the system goes automatically to fail mode: e.g. displays warning icon and/or text that describes the failure. The system immediately goes to special exhaust mode that reduces pressure and temperature via bio-filter to safety conditions.

↓

Step 50: Exhaust: the shredder starts working at low speed. A Top exhaust valve 150 opens to reduce pressure via the bio-hazard filter down to 150kPa (Exhaust Press parameter). When pressure is lower than 150 kPa, a Fast Exhaust valve opens.

↓

Step 60: Drain: Liquids and steam are rapidly exhausted from the chamber to the drain box, until pressure equalizes atmospheric pressure. The shredder's blades typically are operational during this stage.

↓

Step 70: The shredder blades operate at slow speed. Pulses of pressure 100kPa(low)/115kPa(High) in the chamber may be created with periodic operation of the Fast Exhaust valve and Compressed air to chamber valve for 5 minutes. Atmospheric pressure is achieved in the chamber by controlling the Compressed air to chamber and the top Exhaust valves via the bio-hazard filter, until the end of the cycle.

↓

Step 80: Unloading: typically, the chamber rotates to its unloading position (Fig. 1b) and the waste is evacuated to the bin.

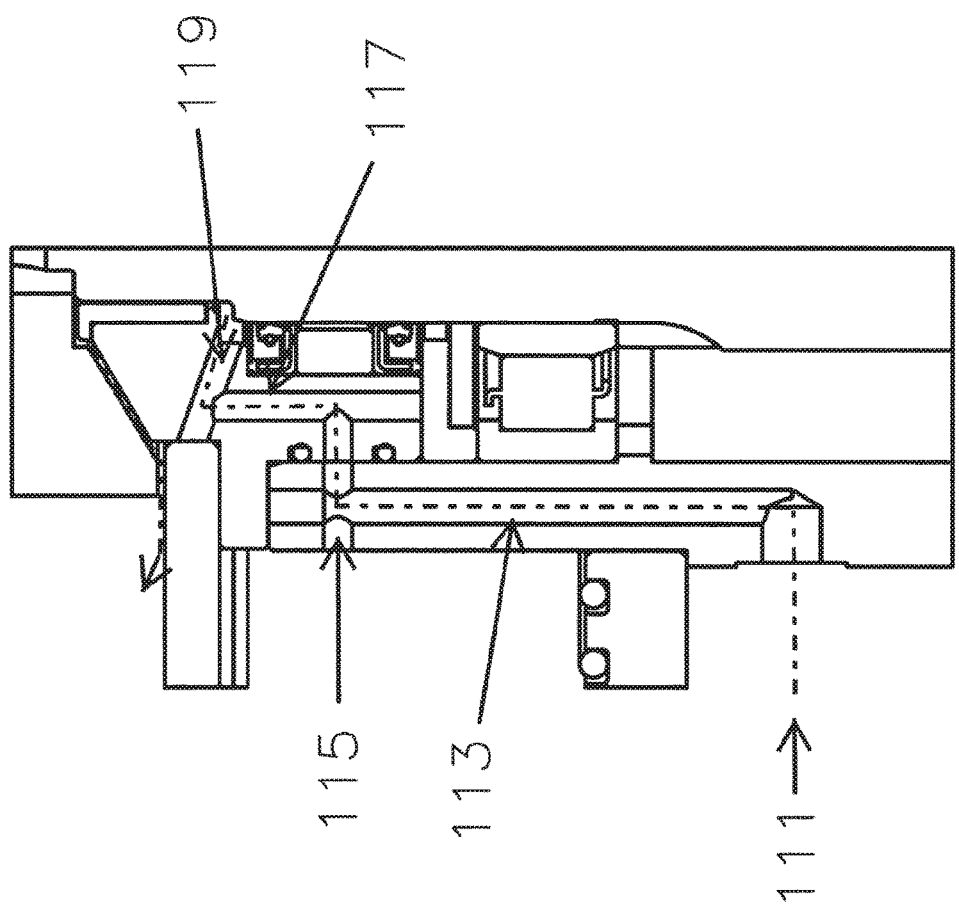

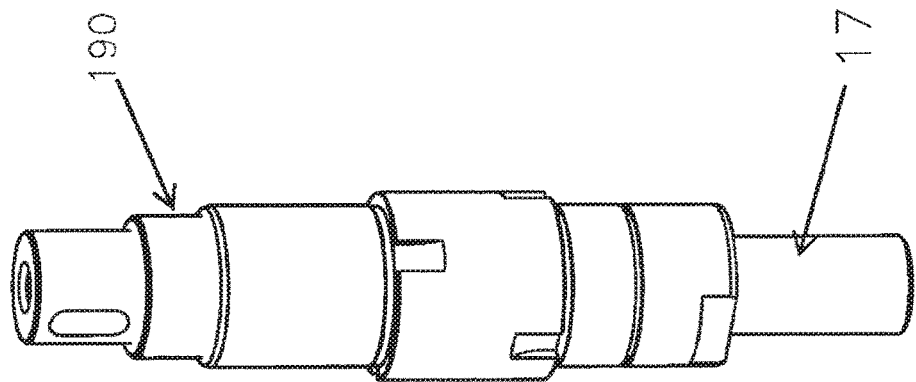
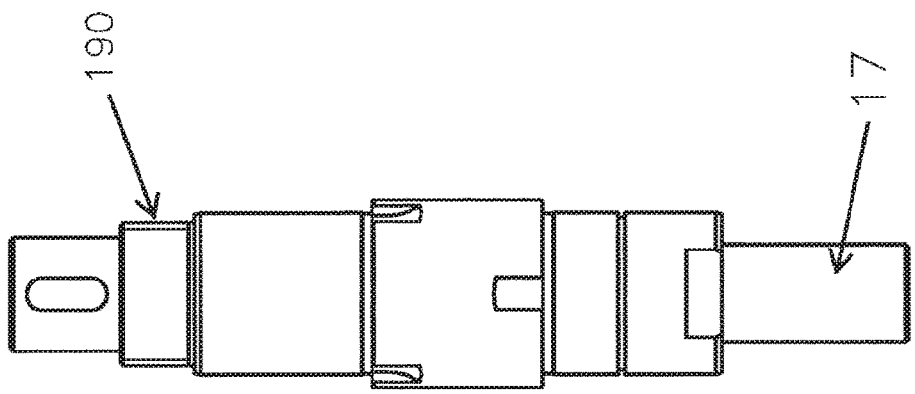
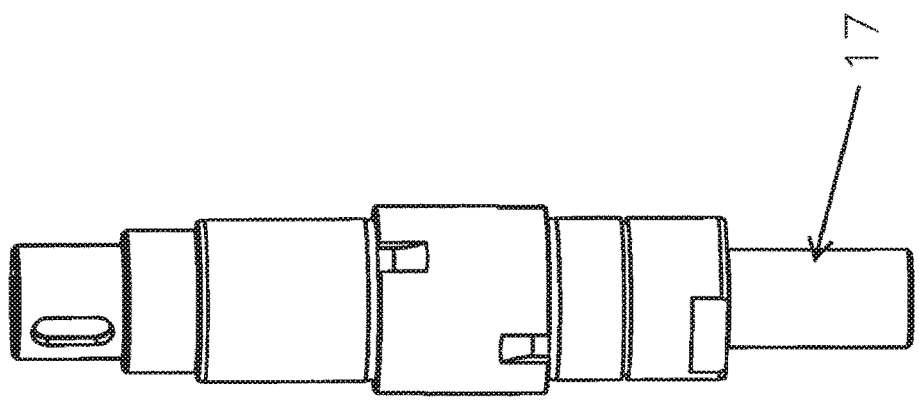

Fig. 11c:

| | |
|---|---|
| 300 | Compressed Air Inlet 6...8 bar Quick Con. for Ø10mm Pa tube |
| 302 | Filter |
| 304 | Pressure Regulator |
| 306 | Pressure Switch CompAir |
| 308 | Main Comp. Air Valve |
| 310 | Regulator 2.0 Bar |
| 312 | Compressed Air |
| 314 | Comp. Air. Chamb. |
| 316 | Bio. Filter Out |
| 318 | Chamber press. 4...20mA |
| 320 | Safety Valve 2.76 Bar |
| 322 | Sprinkler |
| 324 | Filter Temp PT100 |
| 326 | Bio Filter |
| 328 | Vac. Valve |
| 330 | Tap Water Inlet 50µ Filtered 30l/min 1/2" 2-7 bar |
| 332 | Main Water Valve |
| 334 | Separator Valve |
| 336 | Separator |
| 338 | Overflow |
| 340 | Electrode Vac H |
| 342 | Electrode Vac L |
| 344 | Water Reservoir 5L |
| 14 | Booster Pump (B2) Pedrollo PQM 60 |
| 348 | Non return valve |
| 350 | Water Chamb. |
| 352 | Manual flow control valve |
| 354 | Mineral Free Water Inlet from R.O 1/4", 5 micron filtered 4....6 Bar |

Fig. 11d

| 356 | Clean Filter |
|---|---|
| 358 | Steam Chamb. |
| 360 | Ball valve exhaust |
| 362 | Heaters Chamber (H1) 1200W |
| 364 | Strainer Plate |
| 366 | Compressed Air |
| 368 | Seal press. 4...20mA |
| 370 | Chamb. Temp PT100 |
| 372 | Cooling Drain |
| 374 | RO Water |
| 10 | Steam Generator 18kW |
| 378 | Connection for external filtered ventilation. Filtration must be chosen according to local regulations |
| 380 | Flush |
| 382 | Drain Temp PT100 |
| 384 | Electrode Drain |
| 386 | Drain Box |
| 388 | Drain Outlet Ø50mm PVC tube, max. temp 70°C |
| 390 | Vac. Water Val. |
| 392 | VI8 (B1) Water Ring Pump |
| 394 | Regulator 2.0 bar |

Fig. 13c

| 1200 | Mineral Free Water Inlet from R.O 1/4", 5 micron filtered 4....6 Bar |
|------|------|
| 1202 | GenRes Water Valve |
| 1204 | Steam Trap |
| 1206 | Overflow- 12mm |
| 1208 | ResGen High |
| 1210 | ResGen Low |
| 1212 | Strainer |
| 1214 | Water Pump Pedrollo PQM 81 |
| 1216 | Thermostat |
| 1218 | Manual Flush Ball Valve 1/2" |
| 1220 | Heaters 6x2900W |
| 1224 | Heater1 |
| 1226 | Heater2 |
| 1228 | Heater3 |
| 1230 | Heater4 |
| 1232 | Heater5 |
| 1234 | Heater6 |
| 1236 | Electrode GenH |
| 1238 | Electrode GenL |
| 1240 | 4...20Ma Generator Press |
| 1242 | Safety Valve 1/2" 3.5 Bar |
| 1244 | Manometer |
| 1246 | Pressure switch |
| 1248 | Steam Outlet Saturated steam 1/2" max. pressure 3.5 bar, max. temp 170°C |
| 1250 | Manual Ball Valve 1/2" |

Fig. 13d

| | |
|---|---|
| 1302 | Filter And Pressure Regulator |
| 1304 | Pressure Switch Comp Air 12VDC Switching point 5 bar |
| 1306 | Regulator 2.0 Bar |
| 1308 | Pressure Gauge |
| 1310 | To Axial House |
| 1312 | 2/2 Monostabil Main Comp Air Valve |
| 1314 | 24VAC |
| 1316 | Door Piston 1 |
| 1318 | 5/3 Center-Stabil, Door Piston 1 Valve |
| 1320 | Open Door 24VAC |
| 1322 | Close Door 24VAC |
| 1324 | Door Piston 2 |
| 1326 | 5/3 Center-Stabil, Door Piston 2 Valve |
| 1328 | Close Door 2 24VAC |
| 1330 | Open Door 2 24VAC |
| 1332 | Fast Exh. |
| 1334 | 5/2 Mono-Stabil Fast Exh. Valve Operator Valve |
| 1336 | Fast Exh. 24VAC |
| 1338 | Ring Piston |
| 1340 | Ring Safety Piston |
| 1342 | 5/2 Bi-Stabil Ring Piston And Ring Safety Piston Valve |
| 1344 | Door Ring 24VAC |
| 1346 | Close Ring 24VAC |
| 1348 | Fast Exh. Conn. Piston |
| 1350 | 5/2 Bi-Stabil Fast Exh. Conn. Piston Valve |
| 1352 | Connect Exh. 24VAC |
| 1354 | Disrupt. EXH. 24VAC |
| 1356 | Steam Chamb. |
| 1358 | 3/2 Mono-Stabil Steam Chamb. Valve Operator Valve |
| 1360 | Steam Chamb. 24VAC |
| 1362 | Vacuum Valve |
| 1364 | 3/2 Mono-Stabil Vacuum Valve Operator Valve |
| 1366 | Vacuum Valve 24VAC |
| 1368 | Water Chamb. |
| 1370 | 3/2 Mono-Stabil Water Chamb. Valve Operator Valve |
| 1372 | Water Chamb. 24VAC |
| 1374 | 2/2 Mono-Stabil Clean Filter Valve |

| 1376 | Clean Filter 24VAC |
| 1378 | 2/2 Mono-Stabil Comp. Air Chamb.Valve |
| 1380 | Comp. Air Chamb. 24VAC |
| 1382 | Compressed Air Inlet 6...8 Bar |
| 1384 | Ring Close Switch |
| 1386 | Ring Open Switch |
| 1388 | Piston1_In |
| 1390 | Piston2_In | fig. 13e

| MODEL | ISS AC-550 | ISS AC-575 |
|---|---|---|
| Chamber size (mm) Diam D | 500 600 | 500 800 |
| Chamber volume (Ltr) | 110 | 160 |
| Weight (Kg) | 500 | 600 |
| External Dimensions (WxHxD) | 130x200x194 cm | |
| Chamber Door | 1 Automatic Door | |
| Sterilization Temperature | 121°C - 140°C | |
| Steam Source | Saturated Steam | |
| Steam Pressure | 2.5 - 3.5 BAR | |
| Test Pressure | 5.0 BAR | |
| Compressed Air | 5.0 - 7.0 BAR | |
| Water Source Pressure | Filtered Tap Water 1.0 - 6.0 BAR | |
| Power Source | 3-Ph.400 V, 50/60 Hz | |
| Kw including Steam Generator | 16Kw | 25Kw |

Fig. 14a

| Contaminant | Feed water | Condensate |
|---|---|---|
| Evaporation residue | ≤ 10 mg /l | - |
| Silicium oxide, $SiO_2$ | ≤ 1 mg/l | ≤ 0.1 mg / kg |
| Iron | ≤ 0.2 mg/l | ≤ 0.1 mg / kg |
| Cadmium | ≤ 0.005 mg/l | ≤ 0.005 mg/kg |
| Lead | ≤ 0.05 mg/l | ≤ 0.05 mg / kg |
| Rest of heavy metals except Iron, Cadmium, Lead | ≤ 0.1 mg/l | ≤ 0.1 mg / kg |
| Chloride (Cl) | ≤ 2 mg/l | ≤ 0.1 mg / kg |
| Phosphate($P_2O_5$) | ≤ 0.5 mg/l | ≤ 0.1 mg / kg |
| Conductivity (at 25°C) | ≤ 5 ms /cm | ≤ 3 ms /cm |
| pH value | 5 to 7 | 5 to 7 |
| Hardness | ≤ 0.02 mmol/l | ≤ 0.02 mmol/l |
| Appearance | colorless clean without sediment | colorless clean without sediment |

Fig. 14b

| 1. | Separator Valve | Water to Separator |
|---|---|---|
| 2. | Water Chamb. | Water to Chamber |
| 3a. | Steam Chamb. | Steam to Chamber |
| 3b. | Steam | Steam to knife block |
| 4. | Clean Filter | Compressed Air to chamber |
| 5. | Comp. Air Chamb | Compressed Air to chamber |
| 6. | Bio Filter Out | Bio filter to drain |
| 7. | Ball valve Exhaust | Fast Exhaust |
| 8. | Cooling Drain | Cooling to Drain |
| 9. | Vac. Valve | Vacuum, through the Bio Filter |
| 10. | Vac. Water Valve | Separator to Water Pump |
| 11. | Main Water Valve | Main Water Valve |
| 12. | Main Comp. Air Valve | Compressed Air Main valve |

Fig. 14c

| | Component Supplier/producer: | Component Supplier Part number: | Description: |
|---|---|---|---|
| liquid sprinkler 13 | PNR | DDW 2294 B1 | 49000002 DDW 2294 B1 Full cone nozzle |
| vacuum pump 14 | Speck | V18 | 230VAC, 350W, 3,1A |
| control box 16 | CAT Technologies | 06600143 | Control system for Shredder |
| motor 11a | SMEM | SM112M2-2B3 | SM 5,5kW 2p IEC 112 B3 400V 50Hz IP55 |
| motor 11b | SMEM | SM080A4B14 | SM 0,55KW 4P B14 IEC80 400V 50Hz |
| blades 18a | Deqma-Tech Alkatrészgyártó és Kereskedelmi Kft. | MWT15010300003303 | 45200035 Knife Horizontal Mounted 360mmx8mm Thermal Threated Alloy |
| Blades 18b | Deqma-Tech Alkatrészgyártó és Kereskedelmi Kft. | MWT15010300002002 | 45200032 Knife "Z" Shape Ø300mmx6mm Thermal Threated Alloy |
| high-speed rotatable seals 101 | Simrit | 50x65x7 FPM BABSL | high-speed rotatable seals |
| o-ring 102 | Simrit | FPM 62X2,5 | o-ring |

Fig. 14d

|  | Component Supplier/producer: | Component Supplier Part number: | Description: |
|---|---|---|---|
| Pressure Sensor 12a measuring pressure in the lubricant chamber 106 | Xi'an Chinastar M&C Limited | CS-PT1100A 0-6bar | Absolute pressure transmitter, St.st. 0 to 6bar, 4...20mA |
| 12b measuring pressure in main chamber 4 | Xi'an Chinastar M&C Limited | CS-PT1100A 0-6bar | Absolute pressure transmitter, St.st. 0 to 6bar, 4...20mA |
| 12c measuring pressure in steam generator 10 | Xi'an Chinastar M&C Limited | CS-PT1100A 0-6bar | Absolute pressure transmitter, St.st. 0 to 6bar, 4...20mA |

Fig. 14e

SYSTEM AND METHODS FOR CONVERSION OF BIOHAZARD TO MUNICIPAL WASTE

REFERENCE TO CO-PENDING APPLICATIONS

Priority is claimed from U.S. provisional application No. 61/414,071, entitled "Biohazard Waste Disposal System and Methods Useful in Conjunction Therewith" and filed 16 Nov. 2010.

FIELD OF THE INVENTION

The present invention relates generally to medical waste treatment and more particularly to systems for sterilization of medical waste.

BACKGROUND OF THE INVENTION

Conventional technology pertaining to treatment of medical waste is described in the following US patent documents inter alia: U.S. Pat. Nos. 5,078,924; 5,163,375; 5,240,187; 5,236,135; 5,271,892; 5,348,235; 5,362,443; 5,387,350; 5,401,444; 5,458,072; 5,508,004; 5,580,521; 5,639,031; 5,830,419; 5,833,922; 6,039,724; 6,113,854; 7,144,550; 7,718,120; 7,814,851; 7,815,851;

Hospitals and other facilities generate large amounts of medical waste daily. Existing techniques for treatment of medical waste are so unsatisfactory that some health facilities in first-world countries elect to convey only partially neutralized medical waste to poorly regulated third-world countries for disposal, thereby causing dangerous planet-wide pollution. Existing medical waste treating systems are characterized by one or more of the following: large size necessitating a facility located at a distance from the hospital or other waste-generating facility rather than within the hospital; failure to achieve adequate de-contamination; generation of large volumes of waste which are costly to dispose of due to high per-volume disposal costs; generation of a strong, unpleasant odor; requirement for distasteful manual handling e.g. to empty the system's chamber of processed waste which did not exit automatically.

ECODAS is an example of a conventional system that is said to sterilize Regulated Medical Waste (RMW), reduce its volume by 80%, and render its components unrecognizable, by shredding and direct pressurized heated steam all in one enclosed system achieving complete sterilization of infectious materials. The final treated waste is said to be harmless, unrecognizable, and safe for disposal, just like ordinary municipal waste. Shredding is followed by superheated steam (138° C./280° F.) under high pressure (3.8 bars/55 psi) which destroys all forms of microbial life.

The disclosures of all publications and patent documents mentioned in the specification, and of the publications and patent documents cited therein directly or indirectly, are hereby incorporated by reference.

SUMMARY OF THE INVENTION

Certain embodiments of the present invention seek to provide a system for treatment of medical waste in a sterilizer, which uses both vacuum and pressure, whilst cutting the waste, thereby replacing air pockets in the chamber with steam, so as to enhance sterilization.

Certain embodiments of the present invention seek to provide a reason for using vacuum is to replace the air pockets in the chamber with steam so as to achieve sterilization. Typically a mechanism is provided that creates vacuum while cutting, while preventing small parts, glass, metal etc. entering into the sealing of the unit and destroying it.

Certain embodiments of the present invention seek to provide the ability to filter out and drain liquids from a chamber which performs sterilization and shredding, e.g. without shredded sharp matter blocking filters, including liquids accumulating from the treatment and or liquid used to wash the unit.

Certain embodiments of the present invention seek to provide a shaft mechanism which rotates inside an external pressure tank, to prevent bio-hazardous gases/liquids from being exhausted from the main waste treating chamber through the shaft.

Certain embodiments of the present invention seek to provide a mechanism which protects gaskets from dirt or shredded particles e.g. metal/glass/crystals, contact with which during the cycle would damage the gaskets.

Certain embodiments of the present invention seek to provide a compact Integrated Sterilizer & Shredder (ISS) for on-site conversion of biohazard to municipal waste rapidly e.g. in as little as 25 minutes.

The ISS typically performs both size reduction and waste steam sterilization in a single vessel. The vessel is typically fitted with a motor-driven shaft, with shredding/crushing blades. Shredding the waste ensures an acceptable level of sterilization. Shredded waste is typically reduced to as little as 1/10 its original volume, without emitting harmful substances.

The vessel may be supported by two arms which are typically also used to rotate the vessel e.g. for 2 or more of loading (45° e.g.), treatment (0° e.g.) and unloading (135° e.g.) positions. The vessel is typically turned by a motor, and the positions are typically indicated by magnetic switches. The unit typically includes an internal steam generator, automatically controlled by the electronic system. The vessel is typically constructed with internal sprinklers for an automatic cleaning process.

The vessel is typically equipped with a multipurpose shredder/crusher blade on the bottom, regulated by an electric motor which drives the knife shaft. The shaft typically connects the knife to the motor through the bearing housing and the sealing area. The blades are typically mounted on the shaft and are designed to shred waste including some or all of: sharp particles, dialyzers, papers, cloth, plastic and glass.

The blades typically rotate inside the vessel to reduce the size and volume of the waste. Typically, the blades rotate in two alternative directions to avoid textiles and other materials becoming entangled with the blades. Rotation in a second direction e.g. clockwise, untangles and releases whatever may have become wound around the blades when these were previously rotating in a first direction e.g. counterclockwise. For example, software control may provide clockwise rotation for some tens to a few hundred seconds, say, 1 minute, followed by a pause of a few seconds duration, say, a 3 sec pause, followed by a spin of typically approximately the same length, say again a 1 minute spin, in the opposite, counterclockwise, direction, and so on.

The invention shown and described herein includes but is not limited to the following embodiments:

1. A system for treatment of medical waste in a sterilizer, which uses both vacuum and pressure, whilst cutting the waste.

2. A system according to embodiment 1 which is operative to drain liquids which accumulate from the treatment, from a chamber which facilitates sterilization and shredding.

3. A system according to embodiment 1 which is self-washable.

4. A system for treatment of medical waste which includes a shaft mechanism which rotates inside an external pressure tank, thereby to prevent bio-hazardous gases/liquids from being exhausted from the chamber through the shaft.

5. A system for treatment of medical waste which includes a mechanism which protects gaskets from entrance of dirt or shredded particles (metal/glass/crystals) which damage the gaskets during the cycle.

6. A system according to embodiment 1 wherein throughout the process, air is replaced with steam and is evacuated through a bio-filter.

7. A system according to embodiment 6 wherein sterilization with bio-burden of at least 10-6 is achieved (as opposed to disinfectors, which achieve 10-4).

8. Apparatus according to any of the above embodiments wherein the vessel is equipped with a multipurpose shredder/crusher blade on the bottom.

9. Knife apparatus which rotates above 300 RPM inside a chamber which sterilizes medical waste, both with pressure and vacuum, while sterilizing the air which is evacuated while the chamber is contaminated (filtering the bacteria).

10. Apparatus according to embodiment 9 wherein vacuum is used to evacuate the air from the chamber in order to penetrate into the waste (and avoid air pockets), through a bio-filter.

11. A system according to embodiment 2 wherein liquids are drained from a chamber which facilitates sterilization and shredding, through an active filter at the bottom of the chamber.

12. A system according to embodiment 11 wherein water used for the treatment of waste and/or for washing the chamber is sterilized and exits the chamber through the active filter, thereby to obtain dry treated waste.

13. A system for treatment of medical waste which includes a shaft mechanism which rotates inside an external pressure tank, filled with a lubricant.

14. A system according to embodiment 13 wherein the pressure in the tank blocks contaminated gases/liquids from exiting from the chamber through the shaft (both under pressure and under vacuum).

15. A system for treatment of medical waste which includes a mechanism which protects the gaskets from entrance of dirt or shredded particles (metal/glass/crystals) which damages the gaskets during vacuum.

16. Apparatus according to embodiment 8 wherein the blade is regulated by an electric motor which drives the knife shaft.

17. Apparatus wherein the motor is operative to rotate the shaft with a selectable RPM of 300-1400.

18. Apparatus according to any of the above embodiments which performs 5 on-site conversion of biohazard to municipal waste in an order of magnitude of minutes.

19. Apparatus according to any of the above embodiments which performs both size reduction and waste steam sterilization in a single vessel.

20. Apparatus according to any of the above embodiments which includes a motor-driven shaft, with shredding/crushing blades which can rotate in two directions inside a vessel to reduce the size and volume of waste, thereby to provide shredding of the waste which in turn provides sterilization.

21. Apparatus according to any of the above embodiments wherein an internal steam generator (18 KW) is automatically controlled by the electronic system and wherein the vessel is constructed with internal sprinklers for automatic cleaning.

In accordance with an aspect of the presently disclosed subject matter, there is thus provided a system for shredding medical waste, the system comprising a medical waste treating chamber being an interior of an enclosure disposed within an environment which is not to be polluted, a motor, a shredder seated in the chamber and typically including a motor-driven shaft and blades rotated by the shaft, the shaft extending through the enclosure thereby to define an interface between the waste treating chamber and the environment, and interface seal apparatus preventing leakage of at least fluids from the medical waste treating chamber into the environment, via the interface.

In accordance with an embodiment of the presently disclosed subject matter, there is thus further provided a system wherein the interface has an internal end disposed interiorly of the enclosure and an external end disposed exteriorly of the enclosure, and wherein the interface seal apparatus comprises first and second high-speed seals sealing off the internal and external ends of the interface respectively, such that unless the high-speed seals have degraded, the leakage is prevented even when the shredder is operating at high speed.

In accordance with an embodiment of the presently disclosed subject matter, there is thus yet further provided a system comprising a lubricant chamber of pressurized lubricant surrounding, thereby to reduce degradation of the first and second seals and maintained at a pressure which exceeds pressure in the medical waste treating chamber.

In accordance with an embodiment of the presently disclosed subject matter, there is thus yet further provided a system comprising a pressure sensor measuring pressure in the lubricant chamber and alerting for seal degradation if the pressure in the lubricant chamber drops below a predetermined level.

In accordance with an embodiment of the presently disclosed subject matter, there is thus yet further provided a system wherein the medical waste treating chamber is generally cylindrical and has a bottom portion and wherein the shredder is seated in the bottom portion of the medical waste treating chamber, and wherein the motor is external to the medical waste treating chamber and wherein the shredder comprises a rotating shredder and wherein the interface is generally cylindrical.

In accordance with an aspect of the presently disclosed subject matter, there is thus yet further provided a system for shredding and separating liquids from medical waste, the system comprising a medical waste treating chamber, a rotating shredder seated in the chamber, an apertured partition seated below the shredder and having at least one aperture defined therewithin, thereby to partition the chamber into two compartments communicating only via the at least one aperture, and an aperture cleaner below and fixedly associated with the rotating shredder and configured and arranged to sweep non-fluids away from the aperture as the rotating shredder rotates.

In accordance with an embodiment of the presently disclosed subject matter, there is thus yet further provided a system wherein the chamber is cylindrical and has an axis and wherein the aperture cleaner comprises at least one cleaning rod (which may be mounted on or integrally formed with at least one blade of the shredder) which is disposed at a radial distance relative to the axis and which extends from the rotating shredder downward toward the apertured partition and wherein the apertured partition comprises a horizontal plate defining a centered circular track of radius r along which a plurality of apertures are defined and along which the rod travels when the shredder is rotating, thereby to sweep non-fluids away from the plurality of apertures.

In accordance with an embodiment of the presently disclosed subject matter, there is thus yet further provided a system comprising at least one internal liquid sprinkler using sprinkled liquid to provide automatic cleaning of the medical waste treating chamber and wherein the sprinkled liquid travels through the at least one aperture.

In accordance with an embodiment of the presently disclosed subject matter, there is thus yet further provided a system wherein the at least one aperture partition has top and bottom surfaces and the at least one aperture defines a first hole in the top surface and a second hole, in the bottom surface, which is larger than the first hole, thereby to prevent particles from blocking the aperture.

In accordance with an embodiment of the presently disclosed subject matter, there is thus yet further provided a system comprising a vacuum pump operative to eliminate air pockets in the medical waste treating chamber, and a steam generator operative to generate steam in the chamber after the air pockets have been eliminated, thereby to ensure steam sterilization of all waste in the chamber.

In accordance with an embodiment of the presently disclosed subject matter, there is thus yet further provided a system which is also operative for shredding and separating liquids from medical waste, the system comprising an apertured partition seated below the shredder and having at least one aperture defined therewithin, thereby to partition the chamber into two compartments communicating only via the at least one aperture, and an aperture cleaner below and fixedly associated with the rotating shredder, configured and arranged to sweep non-fluids away from the aperture as the rotating shredder rotates.

In accordance with an embodiment of the presently disclosed subject matter, there is thus yet further provided a system comprising a steam delivering conduit leading from the steam generator to an area adjacent the high speed seal thereby to prevent formation adjacent the at least one seal, of a region whose pressure is low, relative to the medical waste treating chamber pressure, which consequently would attract sharp medical waste particles to the seals, low pressure region formation being prevented by steam pressurizing the area adjacent each of the high speed seals just 30 prior to steam pressurization of the medical waste treating chamber.

In accordance with an embodiment of the presently disclosed subject matter, there is thus yet further provided a system comprising a cone embracing the shaft encasing the high speed seals such that if the area's pressure is equal to pressure in the medical waste treating chamber as a whole, sharp medical waste particles do not climb up the cone, hence do not reach the seals.

In accordance with an embodiment of the presently disclosed subject matter, there is thus yet further provided a system wherein external threading is provided on the shaft such that when the shaft rotates and the medical waste treating chamber is pressurized, sharp medical waste particles detrimental to the seals are propelled by the threading, away from the seals.

In accordance with an embodiment of the presently disclosed subject matter, there is thus yet further provided a system wherein the medical waste treating chamber is defined by an enclosure having an opening at its top for introducing medical waste to be treated into the medical waste treating chamber and wherein the system includes a chamber upender to up-end the chamber thereby to remove treated medical waste therefrom via the opening.

In accordance with an embodiment of the presently disclosed subject matter, there is thus yet further provided a system comprising a steam sterilizer operative to steam-sterilize contents of the medical waste treating chamber.

In accordance with an aspect of the presently disclosed subject matter, there is thus yet further provided a method for shredding and separating liquids from medical waste, the system comprising providing a rotating shredder seated in a medical waste treating chamber and an apertured partition seated below the shredder and having at least one aperture defined therewithin, thereby to partition the chamber into upper and lower compartments communicating only via the at least one aperture, and providing an aperture cleaner below and fixedly associated with the rotating shredder and configured and arranged to sweep non-fluids away from the aperture as the rotating shredder rotates.

In accordance with an embodiment of the presently disclosed subject matter, there is thus yet further provided a method including washing the chamber with a fluid which flows into the lower compartment thereby to allow selective removal of the fluid but not of non-fluid waste, from the chamber, via the lower compartment.

In accordance with an embodiment of the presently disclosed subject matter, there is thus yet further provided a method including flushing a fluid through medical waste in the chamber to eliminate malodor, wherein the fluid flows into the lower compartment thereby to allow selective removal of the fluid but not of non-fluid waste, from the chamber, via the lower compartment.

In accordance with an aspect of the presently disclosed subject matter, there is thus yet further provided a method for shredding medical waste, the method comprising providing a medical waste treating chamber being an interior of an enclosure disposed within an environment which is not to be polluted, at least one high-speed seal to seal off the interior from the environment, and providing a vacuum pump operative to eliminate air pockets in the medical waste treating chamber and a steam generator operative to generate steam in the chamber after the air pockets have been eliminated, thereby to ensure steam sterilization of all waste in the chamber, and to generate steam adjacent the seal, thereby to pressurize a region adjacent the seal so as to deter sharp particles within the medical waste, from approaching the seal. A particular advantage of the apparatus of claim 1 is that high speed seals or gaskets can be used and nonetheless are only infrequently, rather than frequently, rendered inoperative hence requiring replacement, due to contact with chemicals, dirt, and shredded metal or glass. Consequently, the shredder's blades can rotate at any suitable speed such as perhaps a speed within the range of, say, 500-1500 rpm, such as, for example, a speed between 1000-1400 rpm, e.g. 1330 rpm, thereby allowing steam to penetrate the waste well enough to achieve a contaminant presence of less than $10\_(-4)$; or more typically less than $10\_(-5)$ or less than $10\_(-6)$. The embodiments referred to above, and other embodiments, are described in detail in the next section.

Any trademark occurring in the text or drawings is the property of its owner and occurs herein merely to explain or illustrate one example of how an embodiment of the invention may be implemented.

The present invention may be described, merely for clarity, in terms of terminology specific to individual products, and the like. It will be appreciated that this terminology is intended to convey general principles of operation clearly and briefly, by way of example, and is not intended to limit the scope of the invention to any particular individual product.

Elements separately listed herein need not be distinct components and alternatively may be the same structure.

BRIEF DESCRIPTION OF THE DRAWINGS

FIGS. 2a-2b, taken together, form a simplified flowchart illustration of an example method of operation for an example ISS (steam sterilizer with an integrated shredder), constructed and operative in accordance with an embodiment of the present invention.

FIG. 5 is a magnification of the bubble 111a drawn in FIG. 4b showing a conduit 111 which is typically the only communication path between the debris in the chamber 4 and the seals 101, all being constructed and operative in accordance with an embodiment of the present invention.

FIGS. 7a, 7b and 7c are respective views of the shaft 17 of FIG. 4b and external threading 190 provided thereupon according to an embodiment of the invention.

FIGS. 11a-d, 12a-12d, 13a-13e, 14a-14e, 15 and 17-18 are illustrations, diagrams and tables describing various embodiments of an example ISS (steam sterilizer with an integrated shredder), for treatment of medical waste.

DETAILED DESCRIPTION OF CERTAIN EMBODIMENTS

Figure 1A:
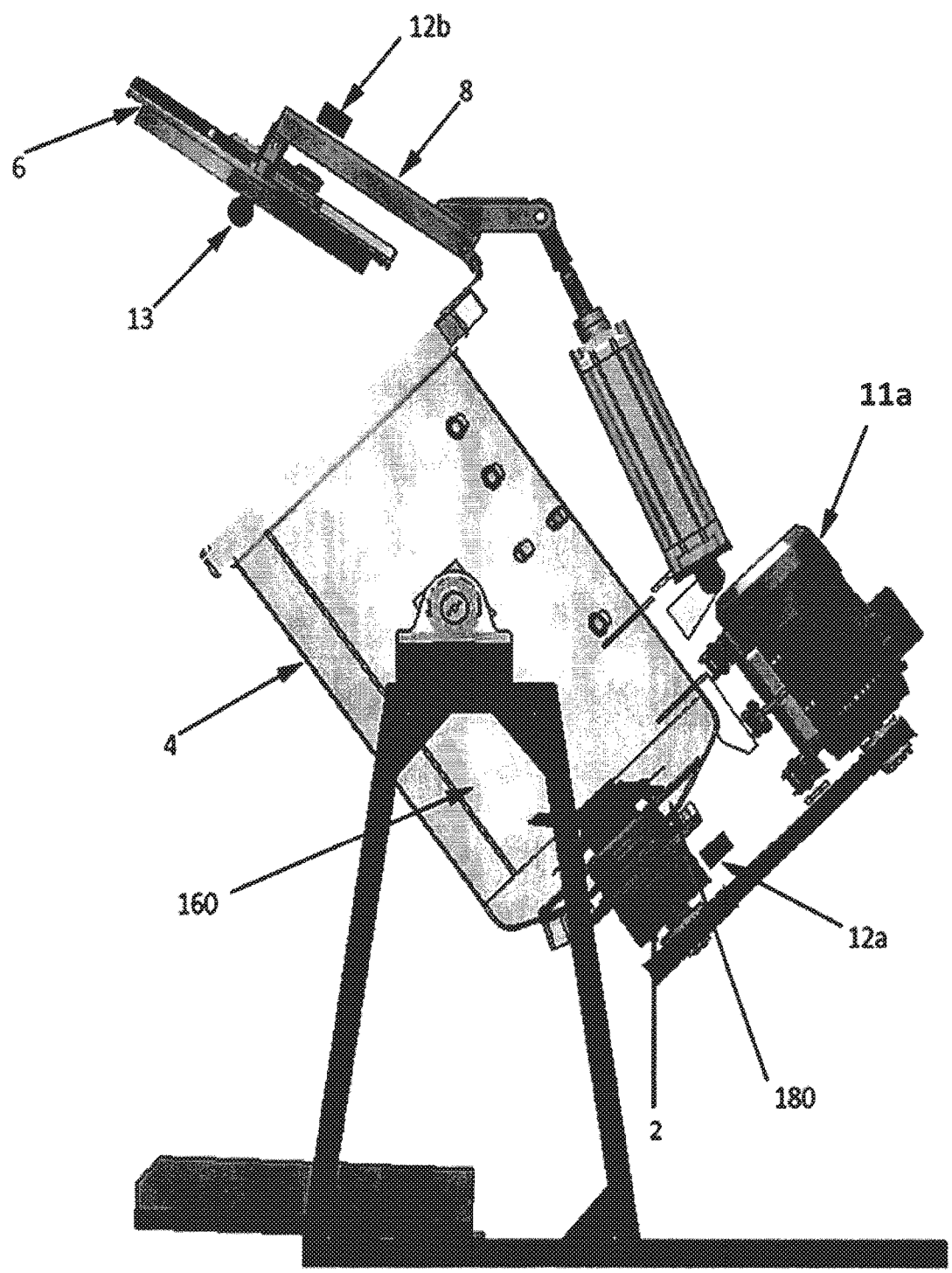
FIGS. 1a-1c are simplified pictorial illustrations of respective possible positions of an Integrated Sterilizer & Shredder (ISS) system for on-site conversion of biohazard to municipal waste, all constructed and operative in accordance with an embodiment of the present invention.
Figure 1B:
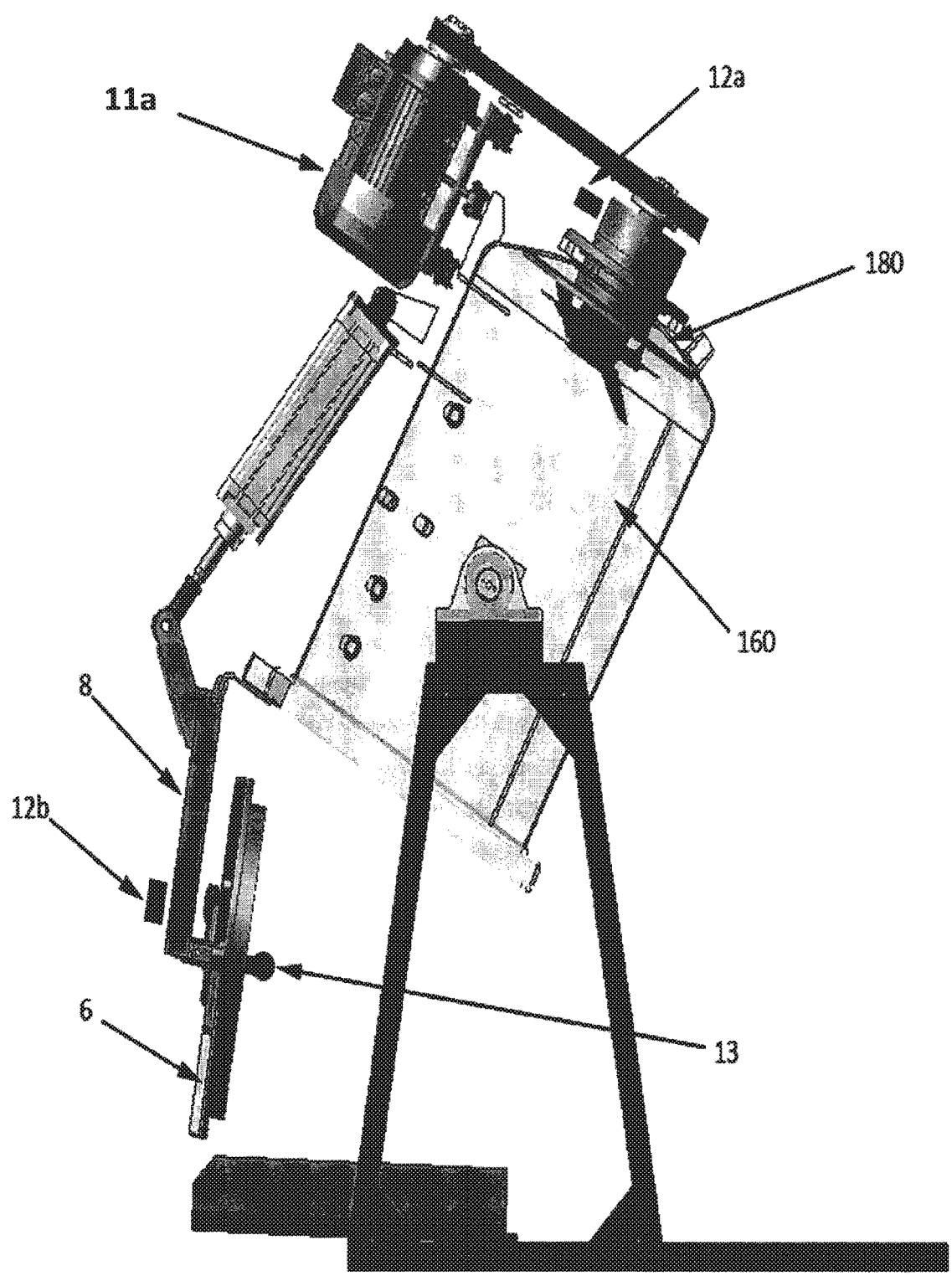
Figure 1C:
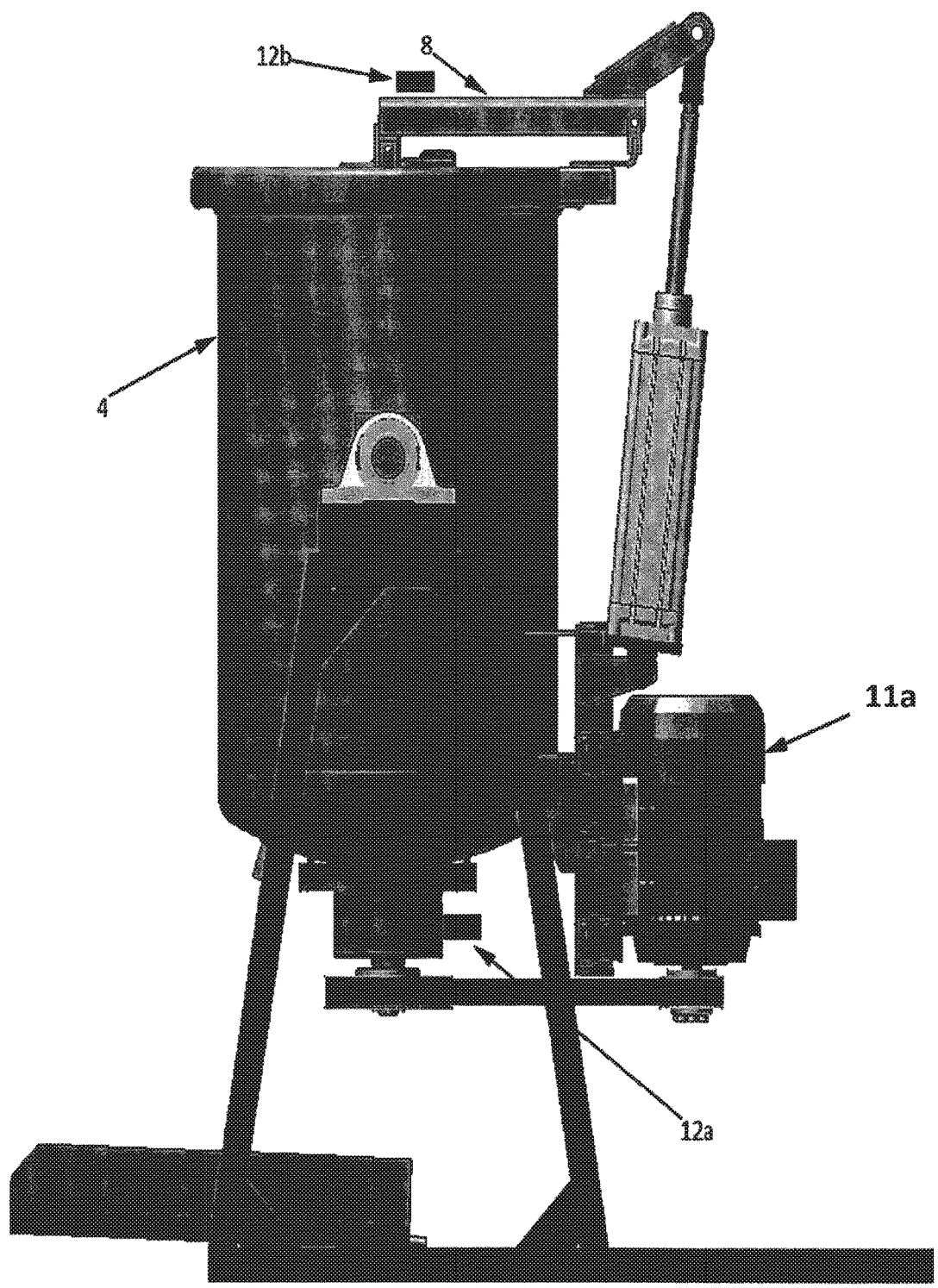

Reference is now made to FIGS. 1a-1c which are simplified pictorial illustrations of respective possible positions of an Integrated Sterilizer & Shredder (ISS) system for on-site conversion of biohazard to municipal waste.

Typically, the system shown and described herein includes some or all of the following subsystems:

a. a medical waste treating chamber being an interior of an enclosure disposed within an environment which is not to be polluted;

b. a shredding subsystem including, typically, a motor external to the medical waste treating chamber and a shredder seated in the chamber and including a motor-driven shaft and blades rotated by the shaft, the shaft extending through the enclosure thereby to define a cylindrical (e.g.) interface between the waste treating chamber and the environment; high-speed seals to seal off the interface; and a lubricant chamber of pressurized lubricant surrounding, thereby to reduce degradation of said first and second seals and maintained at a pressure which exceeds pressure in the medical waste treating chamber.

Typically, a Pressure Sensor 12a (such as, for example, a commercial pressure transducer 0 to 6 bar ABS. cat 514.99012, from Huba control Swiss or perhaps, in certain embodiments, a Xi'an Chinastar M&C Limited, CS-PT1100A 0-6 bar pressure sensor) measures pressure in the lubricant chamber and alerts for seal degradation if the pressure in the lubricant chamber drops below a predetermined level. The first pressure sensor 12a provided for the lubricant chamber is suitably positioned, e.g. as shown in FIG. 4c.

Typically, a steam delivering conduit leads from a steam generator to an area adjacent each of the high speed seals thereby to prevent formation adjacent said seals, of a region whose pressure is low, relative to medical waste treating chamber pressure, which consequently would attract sharp medical waste particles to said seals, low pressure region formation being prevented by steam pressurizing the conduit just prior to steam pressurization of the medical waste treating chamber. Typically, the architecture is such that the only communication path between the debris in the chamber and the seals is via a typically inclined conduit defined by a ramp structure, also termed herein a "cone", such that debris needs to rise along the inclined plane defined by the cone in order to reach the seals. Typically, steam is pushed along the conduit which is the only communication path between the debris in the chamber and the seals to further prevent the debris from reaching the seals. The seals are typically located in an area whose pressure is high relative to the pressure in the chamber such that a pressure gradient prevents debris from reaching the seals. The shaft typically has external threading configured and arranged, e.g. relative to the conduit which is the only communication path between the debris in the chamber and the seals, to carry debris away from the seals as the shaft rotates.

c. a sterilization subsystem typically including a steam sterilizer operative to steam-sterilize contents of the medical waste treating chamber, wherein the sterilizer may include a vacuum pump operative to eliminate air pockets, which resist sterilization, in the medical waste treating chamber; and a steam generator operative to generate steam in the chamber after the air pockets have been eliminated, thereby to ensure steam sterilization of all waste in the chamber.

d. a fluid-utilization and/or straining and disposal subsystem (FIGS. 9a-9f, 10) including an apertured partition seated below the shredder and having at least one aperture defined therewithin, thereby to partition the chamber into two compartments communicating only via the at least one aperture; and an aperture cleaner below and fixedly associated with the rotating shredder and configured and arranged to sweep non-fluids away from said aperture as said rotating shredder rotates—said aperture cleaner comprises at least one cleaning rod (e.g. mounted on or integrally formed with a shredder blade) which is disposed at a radial distance r relative to the axis and which extends from said rotating shredder downward toward said apertured partition and wherein said apertured partition comprises a horizontal plate defining a centered circular track of radius r along which a plurality of apertures are defined and along which the rod travels when the shredder is rotating, thereby to sweep non-fluids away from said plurality of apertures. The above arrangement allows flushing waste to eliminate malodor and/or use of an internal liquid sprinkler (e.g. PNR, DDW 2294 B1) for automatic cleaning of said medical waste treating chamber and wherein said sprinkled liquid travels through said at least one aperture.

A particular advantage of the apertured partition, which is swept free of debris as described above, is that it is effective to partition the waste treating chamber into two compartments such that fluid collects in the lower of the two compartments and non-fluids remain in the upper of the two compartments.

As shown, typically, rather than providing mill-wheels for reducing size of bio-hazardous matter, a shredder 2 is provided within a chamber 4 which holds the bio-hazardous waste to be converted. A particular advantage of certain embodiments is that the shredder allows the chamber to be more compact than the mill-wheels would; since mill-wheels both occupy space and typically require a double allocation of space for the bio-hazard, both above the wheels for pre-milled waste material and below the wheels for milled waste material. A motor 11a, typically external to the chamber 4, drives the typically rotational motion of the shredder 2 blades. Once waste has been shredded, a steam generator 10 supplies steam to the chamber, thereby to effectively, due to the small size of the shredded particles, steam-sterilize contents of the medical waste treating chamber.

Figure 9A:
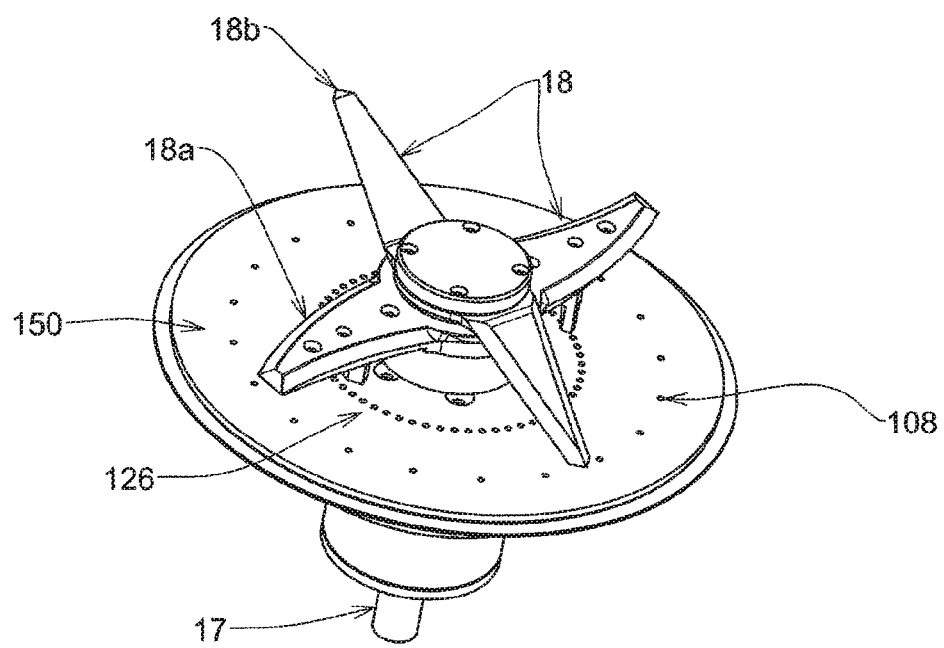
FIGS. 9a-9f, 10 are respective views of components of a fluid straining and disposal subsystem including an apertured partition operative to partition a waste treating chamber into two compartments such that fluid collects in the lower of the two compartments and non-fluids remain in the upper of the two compartments, all as constructed and operative in accordance with an embodiment of the present invention.
Figure 9B:
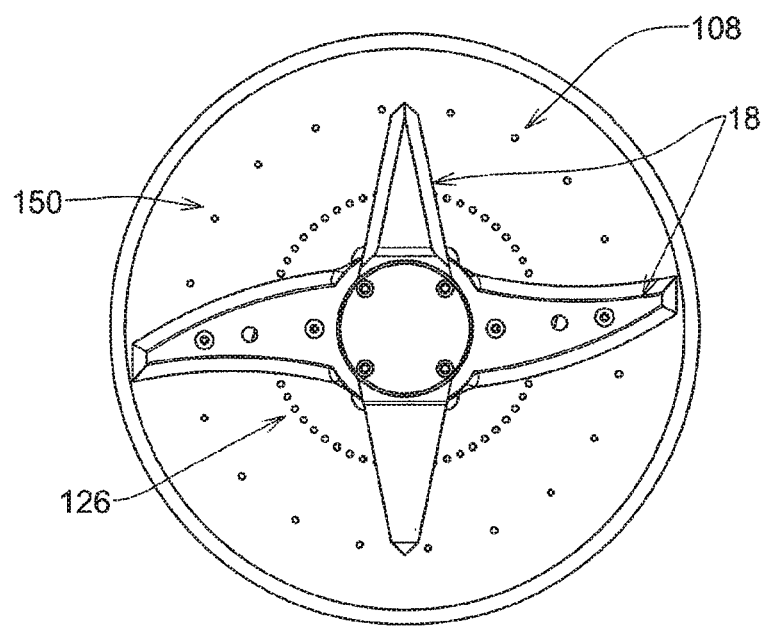
Figure 9C:
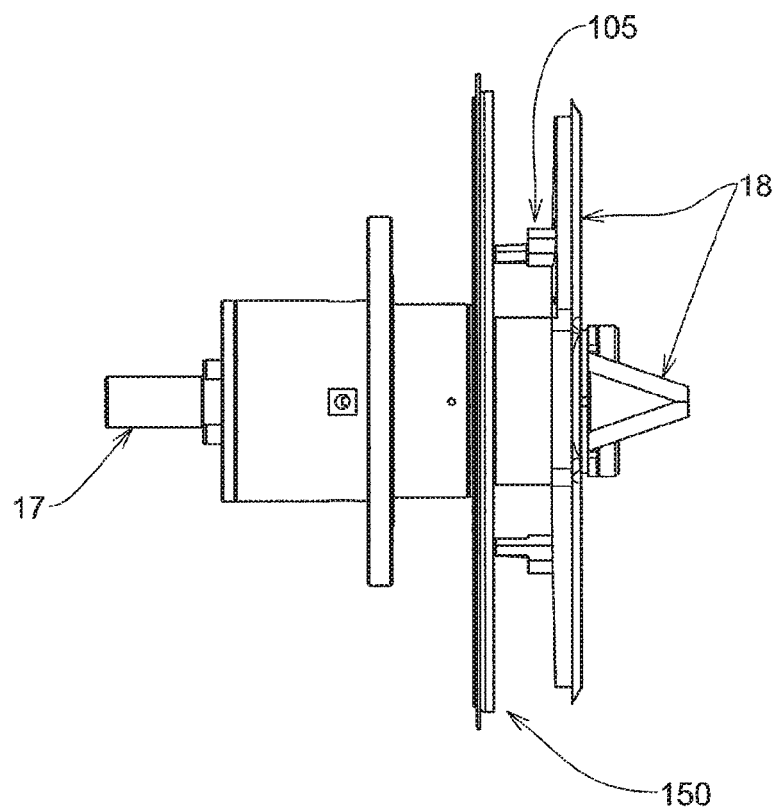
Figure 9D:
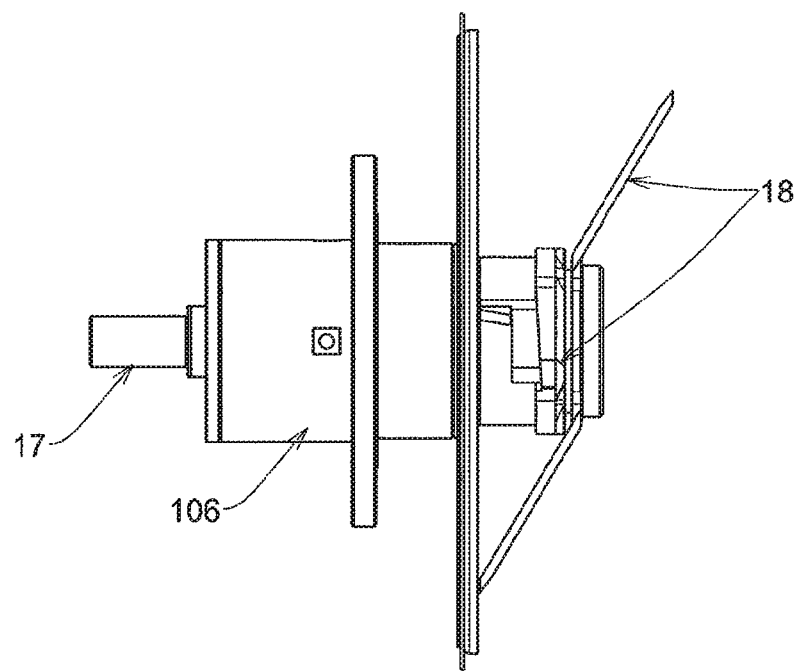
Figure 9E:
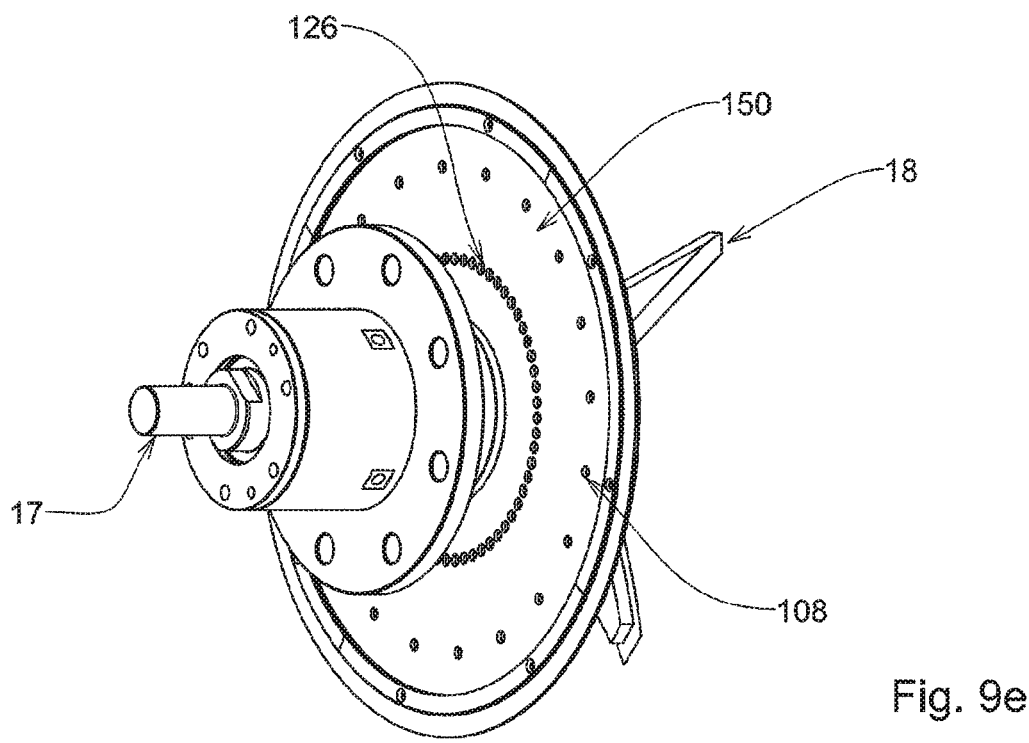
Figure 9F:
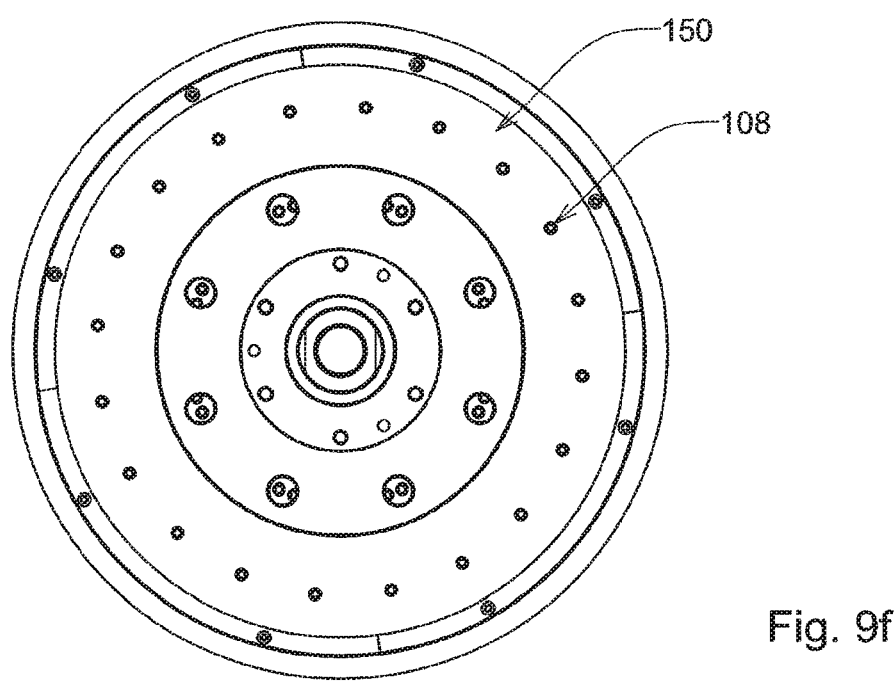
Figure 10:
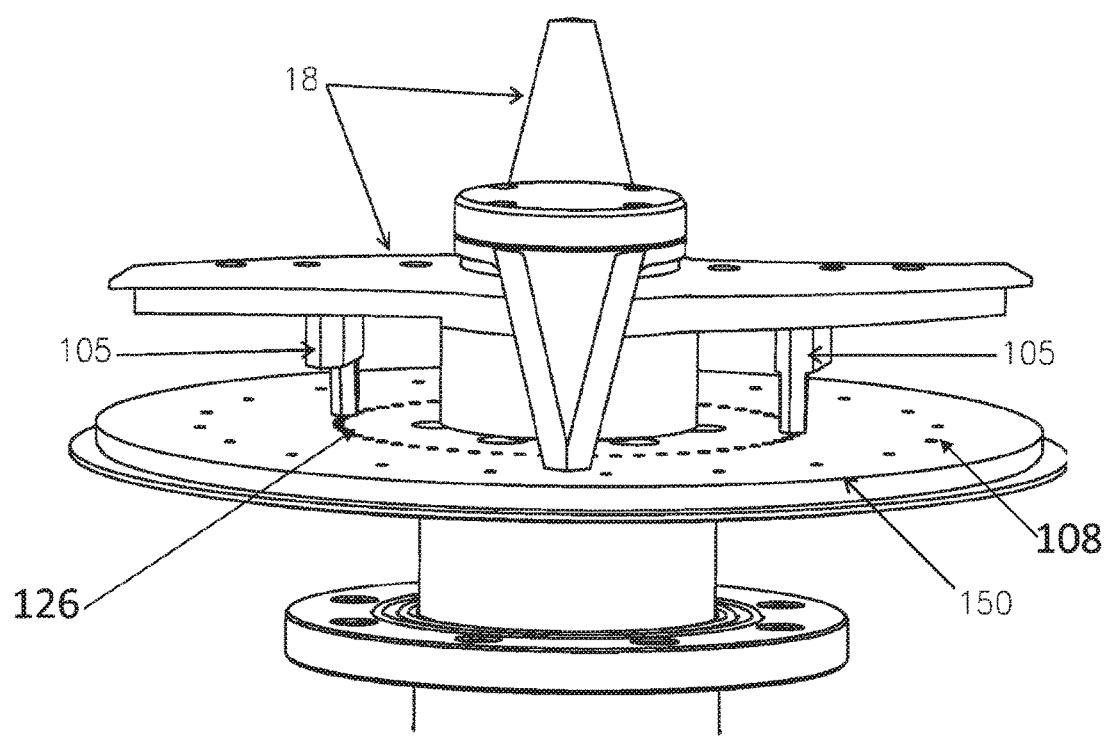

It is appreciated that medical waste treating chamber 4 typically comprises an interior of an enclosure disposed within an environment which is not to be polluted. Shredder 2, seated in the chamber 4, typically includes a shaft 17 driven by a motor 11 and at least one blade assembly 18 rotated by the shaft 17. According to certain embodiments, at least one and typically more than one blade assembly 18 is provided, typically including a horizontal blade 18a and a top blade 18b, e.g. as shown in FIG. 9a.

If the motor 11a is external to the medical waste treating chamber 4, the shaft extends through the enclosure thereby to define a cylindrical (e.g.) interface between the waste treating chamber and the environment.

Typically, another motor, termed herein "motor 11b" and not shown, turns the chamber 4 up-side down and then back up again. The door 6 of the chamber 4 may be operated by a cylinder (pneumatic system).

Typically, high-speed rotatable seals 101 are used to seal the cylindrical interface off thereby maintaining complete isolation of the waste treating chamber's interior, relative to the environment. Typically, a chamber or tank 106 of pressurized lubricant surrounds the seals, thereby to reduce degradation thereof. The lubricant, which may for example comprise a suitable oil, such as but not limited to a conventional high temperature (180 degrees C.) oil lubricant, may be maintained at a pressure which exceeds pressure in the medical waste treating chamber.

Typically, a Pressure Sensor 12a is provided for measuring pressure in the lubricant chamber 106 and alerting for seal degradation if the pressure in the lubricant chamber drops below a predetermined level.

According to certain embodiments, an apertured partition (also termed herein "hole plate" or "strainer plate") 150 (FIGS. 9a-9f, 10) is seated below the shredder and has at least one aperture 108 defined therewithin, thereby to partition the chamber into two compartments, an upper compartment 160 which retains non-fluid material and a lower compartment 170 for accumulating and drawing off liquid, which communicates with the upper compartment only via the at least one aperture. Each aperture 108 typically is generally conical in configuration with the wide end pointing downward, e.g. as shown.

Typically, an aperture cleaner 105 (which may for example be formed of or mounted on a shredder blade) is disposed below and fixedly associated with the rotating shredder and is configured and arranged to sweep non-fluids away from said aperture as said rotating shredder rotates. Aperture cleaner 105 comprises at least one cleaning rod (or a pair of such rods, as indicated by the two reference numerals 105 in FIG. 10), which is disposed, e.g. held by a radial arm, at a radial distance r relative to the axis of rotation of the shredder 2 and which extends downward from the shredder 2 toward said apertured partition 150.

Typically, an internal liquid sprinkler (FIG. 11a) is provided which uses sprinkled liquid to provide automatic cleaning of said medical waste treating chamber and/or to flush waste so as to eliminate malodor. The sprinkled liquid travels through said at least one aperture, thereby accumulating in the bottom compartment for selective liquid-only evacuation from the chamber 4, e.g. to the local sewer system, such that non-liquids which are ineligible to enter the sewer system, remain inside the chamber.

Typically, vacuum is created in the chamber 4 before steam is introduced, so as to eliminate air pockets which would compromise the efficacy of the steam sterilization. A vacuum pump 14 (e.g. Speck, VI 8) may be provided for this purpose. The steam generator 10 (e.g. such as the example steam generator shown in FIG. 13a) may then generate steam in the chamber, after the air pockets have been eliminated, thereby to ensure steam sterilization of all waste in the chamber 4.

Typically, a cone 107 (also termed herein "ramp channel" 107) whose apex faces upward embraces the shaft 17, encasing the high speed seals 101, such that if the pressure adjacent the seals is equal to pressure in the medical waste treating chamber as a whole, sharp medical waste particles nonetheless do not reach said seals because they do not climb up the cone.

Typically, a steam delivering conduit leads from steam generator 10 to an area adjacent each of said high speed seals 101, e.g. the area encased by cone 107, thereby to prevent formation adjacent said seals, of a region whose pressure is low, relative to medical waste treating chamber pressure. If a low-pressure region were to form adjacent the seals, this region would attract sharp medical waste particles to said seals 101. Low pressure region formation is prevented by steam pressurizing the area adjacent each of said high speed seals 101 to create a pressure gradient sufficient to keep any sharp matter away from the seals, just prior to steam pressurization of the medical waste treating chamber 4.

Steam generator 10 may comprise a Tuttnauer Israel 18 KW electrical steam source or any other suitable steam source. Steam generator 10, vacuum pump 14, and a control box 16 which controls operation of the apparatus as a whole, are typically not location sensitive. An example implementation of control box 16 is provided herein with reference to FIGS. 12*a*-12*d*, 17 and 18. An example implementation of steam generator 10 is shown in FIG. 13*a*.

A first pressure sensor 12*a* may be provided for the lubricant chamber and is suitably positioned, e.g. as shown in FIG. 4*c*. A second pressure sensor 12*b* may be provided for the waste chamber and is suitably positioned, e.g., as shown, on the right side on top of the holder 8 of the door 6 of the chamber 4; the sprinkler 13 may point downward from the bottom surface of the middle of the cover or door of the chamber 4. A third conventional pressure sensor termed herein "sensor 12*c*" may be provided for the steam pressure source, which may be a separate unit which is not integrally formed with the waste chamber.

Motor 11*a*, operating the blades of the shredder 2, may for example comprise an SMEM, SM112M2-2B3 (5.5 kW 2p IEC 112 B3 400V 50 Hz IP55). A suitable separate Motor e.g. SMEM, SM080A4B14 (0.55 KW 4P B14 IEC80 400V 50 Hz), may move the waste chamber from one to another of its orientations as shown in FIGS. 1*a*-1*c*.

An example method of operation (Cycle Sequence) for the system shown and described above is now described with reference to FIG. 11*a*. The method may include some or all of the following steps or stages, suitably ordered e.g. as follows:

Loading: waste is loaded into the chamber 4, chamber's door closes. Then, chamber rotates to process position e.g. fully vertical as shown in FIG. 1*c*.

Shredding: The shredder 2 starts working with the start of the cycle at different speeds, as required. The shredder 2 continues working in high speed for 2 minutes. After this time elapses, the shredder 2 stops working.

Sterilization: The cycle starts with one vacuum pulse to 35 kPa, to remove the air from the chamber 4.

Heating: Steam is introduced into the chamber until sterilization temperature is reached, e.g. 134° C. and pressure of 312 kPa. Temperature and pressure are controlled at the required sterilization level for the duration of sterilization.

A Bio Filter valve (VI in FIG. 11*a*) typically operates in shoot mode e.g. 3 seconds opened and 30 seconds closed, throughout the sterilization stage.

Exhaust: the shredder starts working at low speed. A top exhaust valve 150 opens to reduce pressure via the bio-hazard filter of FIG. 11*a* down to 150 kPa (Exhaust Press parameter). When pressure is lower than 150 kPa, a fast exhaust valve opens.

Drain: Liquids and steam are rapidly exhausted from the chamber to the drain box, until pressure equalizes atmospheric pressure. The shredder's blades typically are operational in this stage.

Figure 11A:
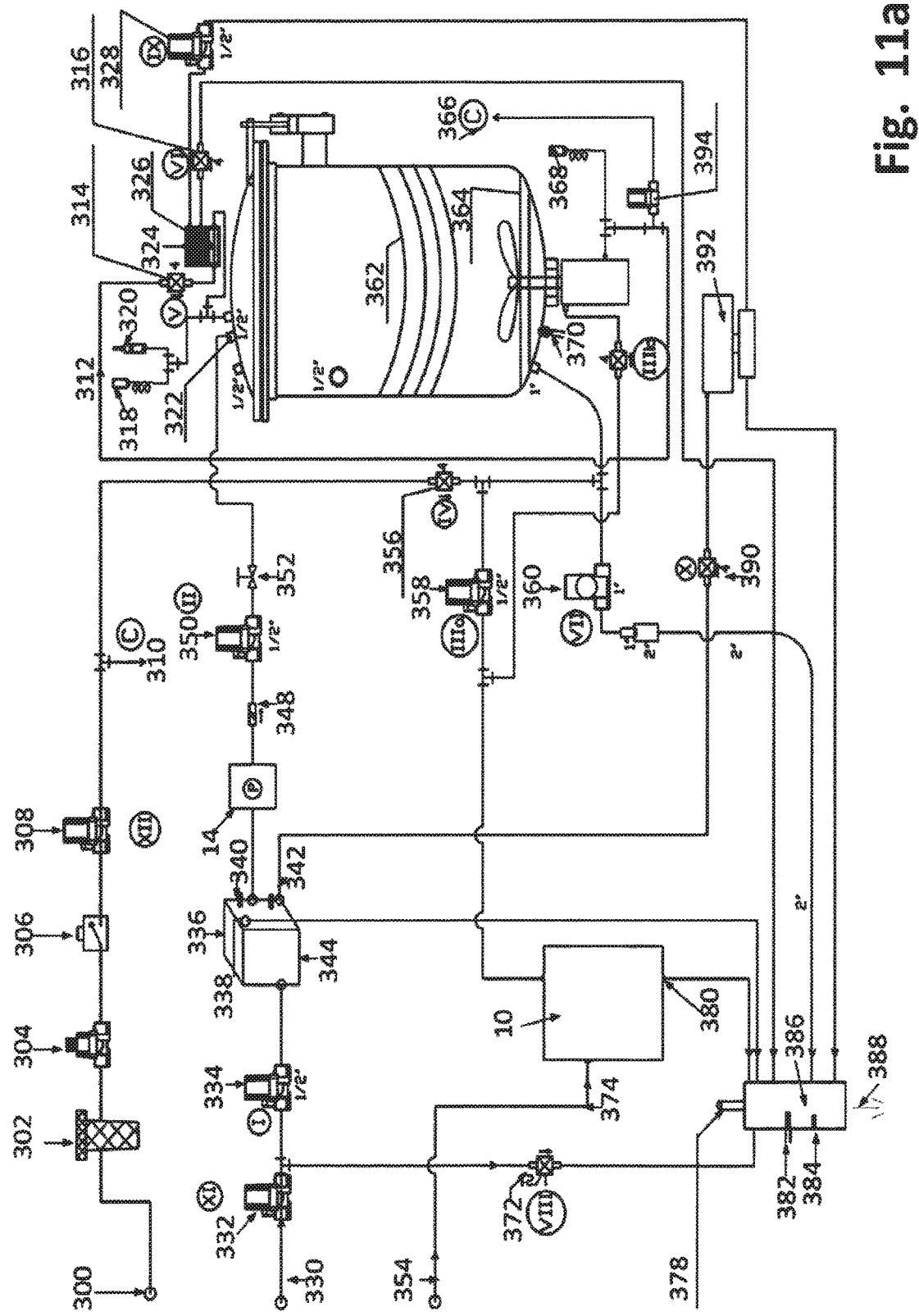

Drying: vacuum is created in the chamber for 5 min During the drying stage, the Bio-Filter out valve VI of FIG. 11*a* may operate in shoot mode of 2 seconds On and 45 seconds Off. Atmospheric pressure is achieved in the chamber by controlling the compressed air to chamber and the top exhaust valves via the bio-hazard filter, until the end of the cycle.

Unloading: typically, the chamber rotates to its unloading position (FIG. 1*b*) and the waste is evacuated to the bin.

An example method of operation of the system of the present invention is shown in FIGS. 2*a*-2*b*. The method of FIGS. 2*a*-2*b* typically includes some or all of the following steps, suitably ordered e.g. as shown; it is appreciated that all parameter values are merely exemplary since these values may be determined by a person skilled in the art:

Step 15: Loading: waste is loaded into the chamber 4, chamber's door closes. Then, chamber rotates to process position e.g. fully vertical as shown in FIG. 1*c*.

Step 20: Shredding: The shredder 2 starts its operation, typically at different speeds, as appropriate to the application. For example, the shredder may initially operate back/forward at high speed, e.g. 3 seconds forward, 3 seconds backward, for 3 minutes, and then subsequently may operate 30 seconds forward, 30 seconds backward, again at high speed till exhaust stage (step 50 below).

Step 30: Prevacuum: The cycle starts with one vacuum pulse to 35 kPa, to remove the air from the chamber 4.

Step 40: Heating: Steam is introduced into the chamber until sterilization temperature is reached, e.g. 134° C. and pressure of 312 kPa. temperature and pressure are controlled at a suitable sterilization level for the duration of sterilization. A Bio Filter valve (e.g. VI in FIG. 11*a*) typically operates in shoot mode e.g. 3 seconds opened and 30 seconds closed, throughout the sterilization stage.

Step 45: Sterilization: Temperature and pressure are maintained at a suitable 30 level, e.g. 134°+4° and 312 kPa+28 kPa, for 5 minutes.

Cycle fail: If during the sterilization process, the cycle fails, the system goes automatically to fail mode: e.g. displays warning icon and/or text that describes the failure. The system immediately goes to special exhaust mode that reduces pressure and temperature via a bio-filter to safety conditions.

Step 50: Exhaust: the shredder starts working at low speed. A Top exhaust valve 150 opens to reduce pressure via the bio-hazard filter (e.g. as shown in FIG. 11*a*) down to 150 kPa (Exhaust Press parameter). When pressure is lower than 150 kPa, a Fast Exhaust valve opens.

Step 60: Drain: Liquids and steam are rapidly exhausted from the chamber to the drain box, until pressure equalizes atmospheric pressure. The shredder's blades typically are operational during this stage.

Step 70: The shredder blades operate at slow speed. Pulses of pressure 100 kPa (low)/115 kPa (High) in the chamber may be created with periodic operation of the Fast Exhaust valve and Compressed air to the chamber valve for 5 minutes. Atmospheric pressure is achieved in the chamber by controlling the Compressed air to chamber and the top Exhaust valves via the bio-hazard filter, until the end of the cycle.

Step 80: Unloading: typically, the chamber rotates to its unloading position (FIG. 1*b*) and the waste is evacuated to the bin.

EXAMPLE

The ISS may be constructed of carbon steel and have a total height of 2 m. The cylindrical (e.g.) vessel may be constructed of Stainless Steel 316 L, 160 liters (150 liters net) for 16-25 Kg, with one automatic hinge door. The motor is of 5.5 kW and is sufficient to rotate the shaft with an RPM of 300-1400 for various operations. The blade is made of high carbon steel with hardened cutting edges. Technical Specifications may be as stipulated in the table of FIG. 14*a*. The example system typically complies with some or all of the following standards & directives:

EN 60204-1, Safety of machinery—Electrical equipment of machines—General requirements;

EN 61000-6-2 Electromagnetic compatibility (EMC)—Generic standards—Immunity for industrial environments;

EN 61000-6-4 Electromagnetic compatibility (EMC)—Generic standards—Emission standard for industrial environments.

Machinery Directive-2006/42/EC; Pressure Equipment Directive-PED 97/23/EC; EMC Directive 89/336/EEC Article 7 (1); Low Voltage Equipment Directive 2006/95/EC.

Quality Management System Standard: ISO 9001: 2008.

Figure 3A:
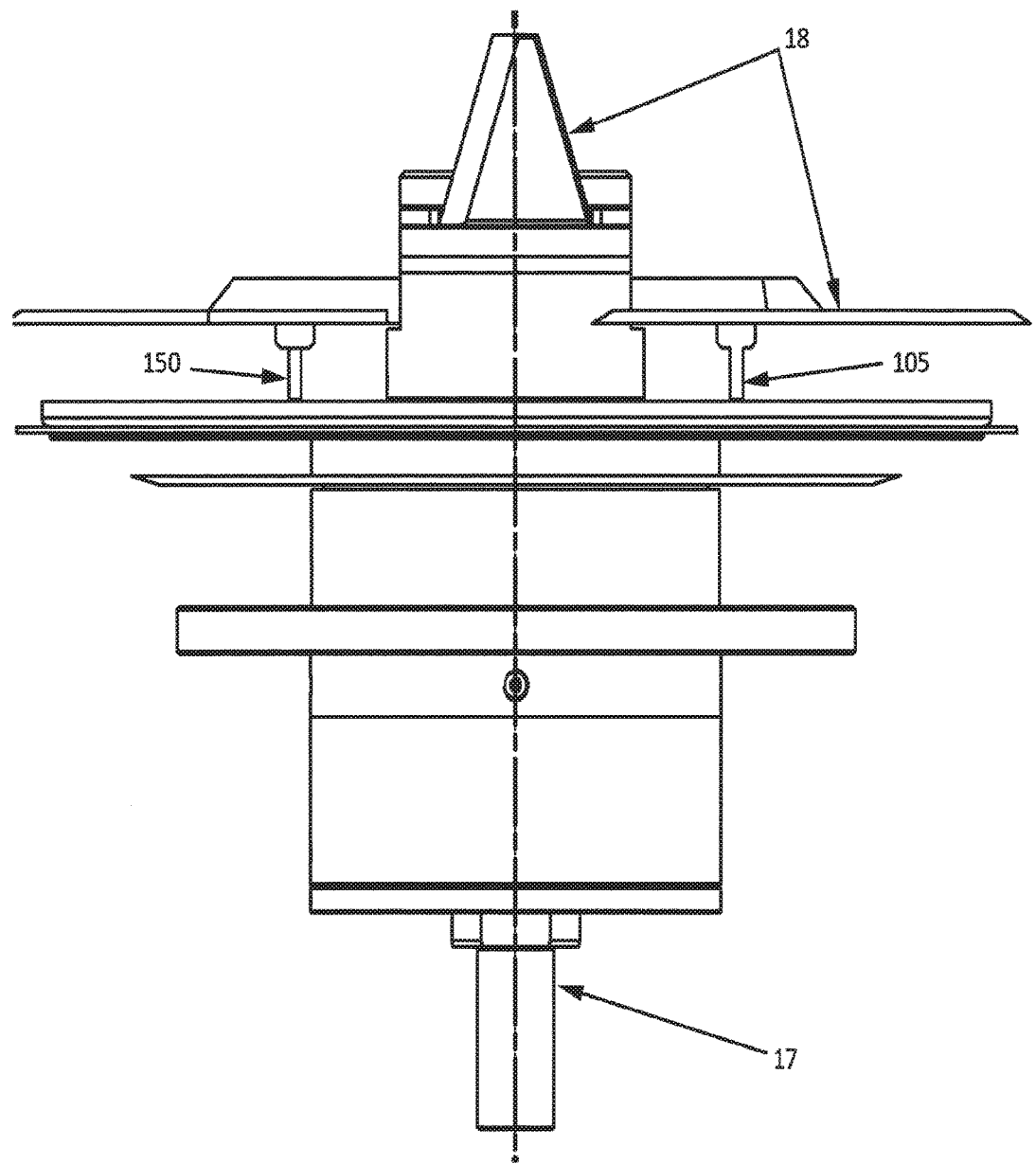
FIGS. 3a and 3b illustrate a knife block or "knife module" performing the shredding functionality of the system of FIGS. 1a-1c, the module including blades as well as associated elements providing rotation such as bearings and gaskets, all constructed and operative in accordance with an embodiment of the present invention.
Figure 3B:
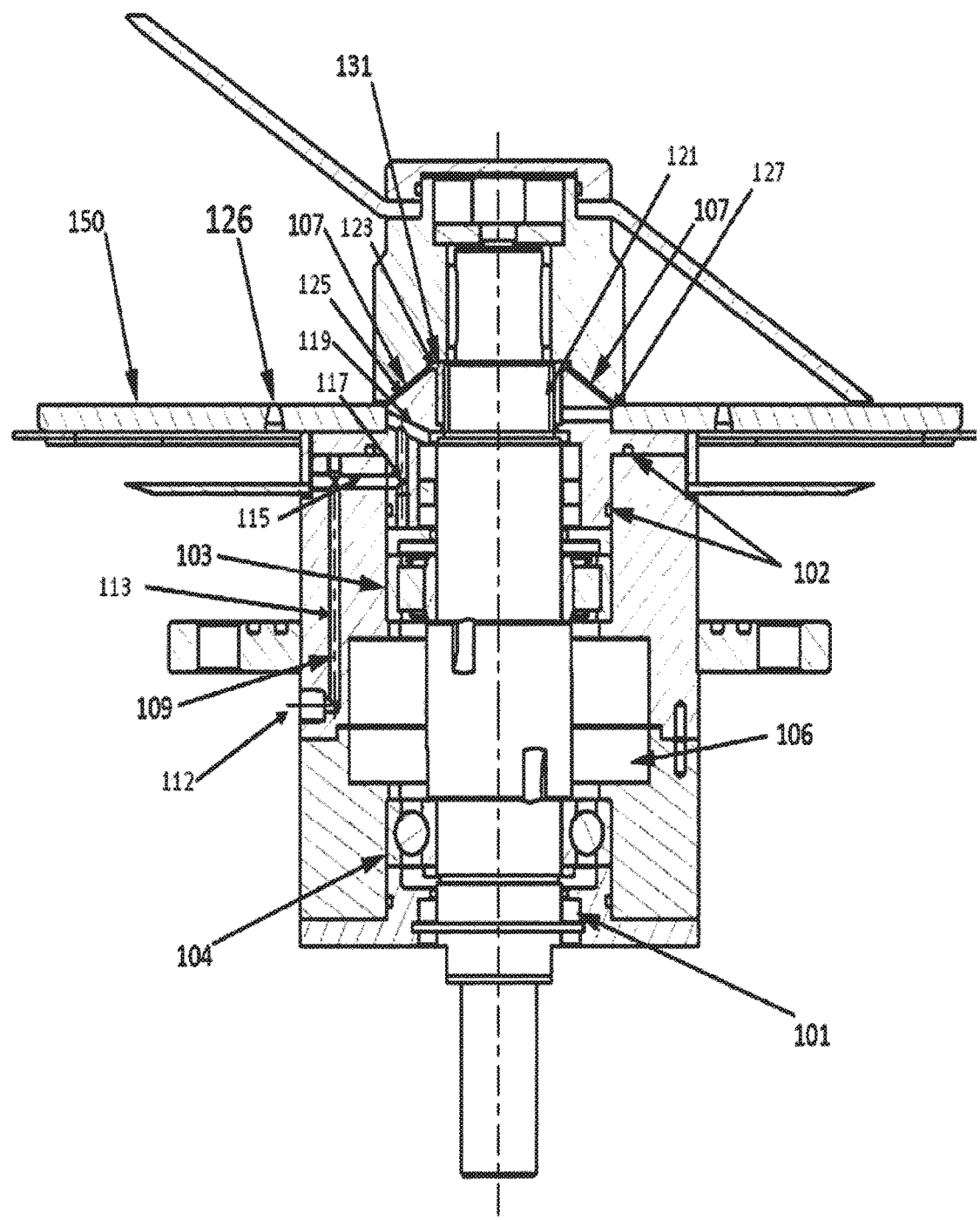

FIGS. 3a and 3b are side and cross-sectional views of a knife block and associated lubricant chamber, constructed and operative in accordance with certain embodiments of the present invention.

Figure 4A:
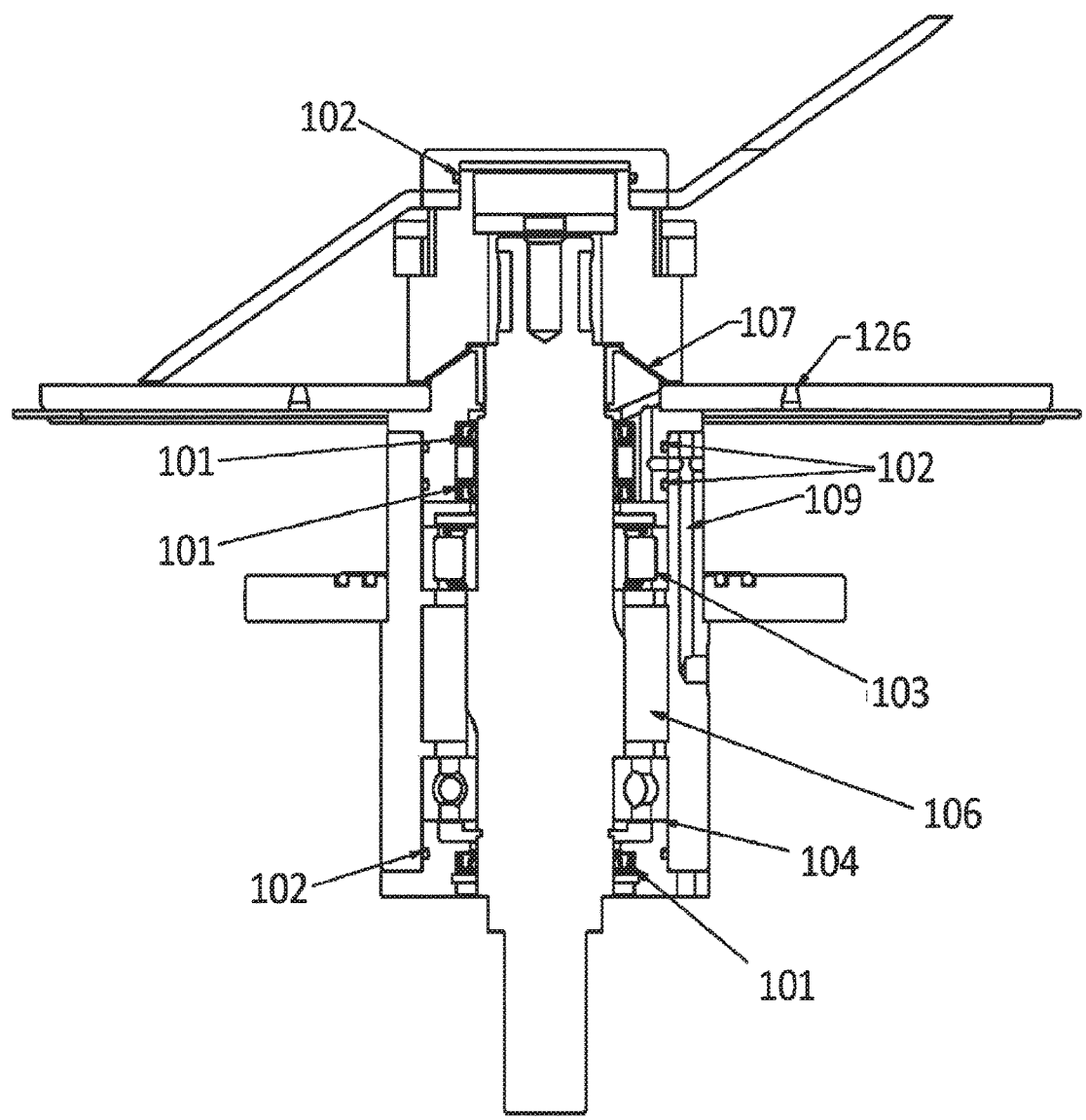
FIGS. 4a-4c are respective sectional, cut-away isometric and isometric illustrations of a bottom portion of an integrated steam sterilization and shredding system according to an embodiment of the invention which is particularly suited to preventing debris, particularly sharp particles, from contacting high speed seals 101 which seal off the chamber 4, at the location in which the shaft 17 extends through the wall of the chamber 4.
Figure 4B:
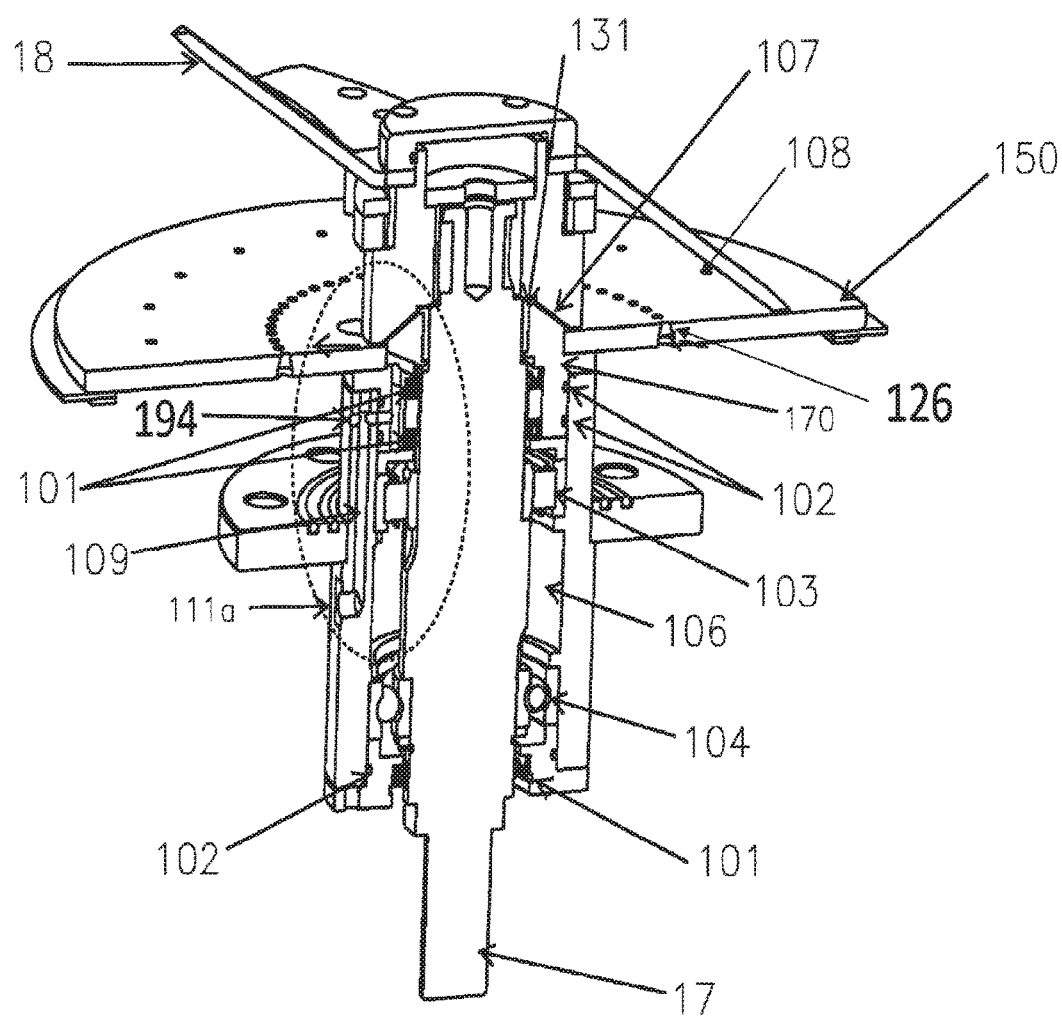
Figure 4C:
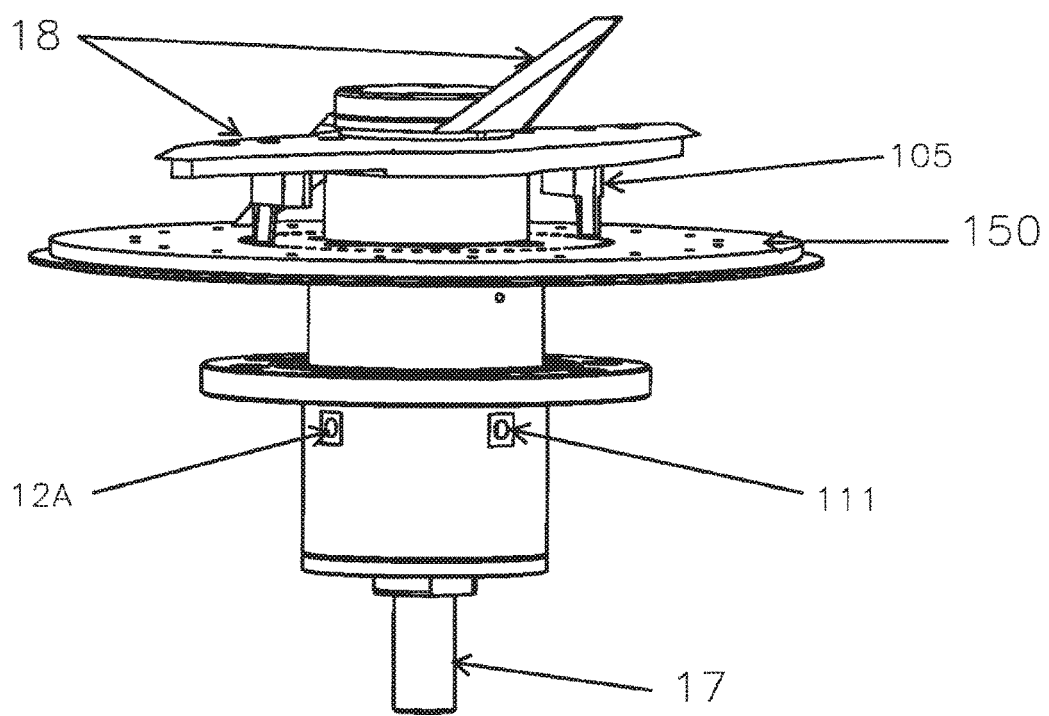

FIGS. 4a and 4b are respective sectional and isometric illustrations of a bottom portion of an integrated steam sterilization and shredding system according to an embodiment of the invention which is particularly suited to preventing debris, particularly sharp matter, from contacting high speed rotatable seals 101 which seal off the chamber 4, at the location in which the shaft 17 extends through the wall of the chamber 4.

O-rings 102 provide a seal between the knife block's upper and lower portions, preventing escape of the lubricant and reduction of pressure in the lubricant chamber. Cylindrical roller bearing 103 and deep groove ball-bearing 104 facilitate rotation of the shaft rotate about its axis; bearing 103 copes with radial stresses and bearing 104 functions as a holder bearing.

Figure 6B:
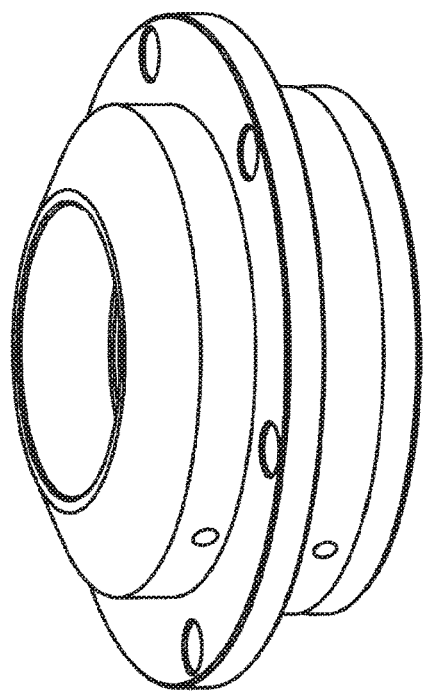
FIGS. 6a and 6b are respective cut-away perspective and perspective views of the cone 107 of FIG. 4b, according to an embodiment of the invention.
Figure 6A:
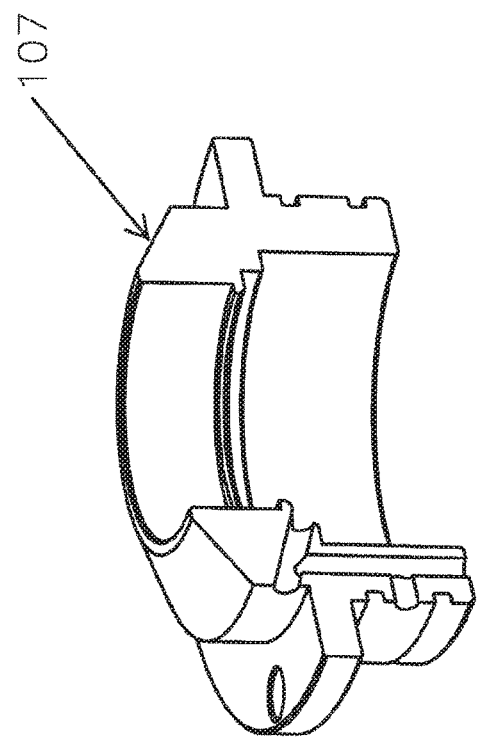

FIG. 5 is a magnification of the bubble 111a drawn in FIG. 4b showing a conduit 111 which is typically the only communication path between the debris in the chamber 4 and the seals 101. FIGS. 6a and 6b are respective views of the cone 107 of FIG. 4b, according to an embodiment of the invention. FIGS. 7a-7c are respective views of the shaft 17 of FIG. 4b and external threading 190 provided thereupon according to an embodiment of the invention.

The bronze sleeve 131 generates a narrow steam-supplying channel, typically of less than 1 mm (e.g. approximately 0.5 mm) in diameter, between itself and the shaft. If the shaft rotates in a first, "forward" (e.g. clockwise) direction, together with the knives, then whenever any particles enter this gap, the rotation has the effect of pushing these back into the waste chamber, thereby preserving the cleanliness of the knife block and preventing malfunction as a result of blockage.

As shown in FIGS. 3 and 4b, 5, 6a-6b and 7a-7c inter alia, a steam delivering path typically leads from a steam generator to an area adjacent each of the high speed seals 101 thereby to prevent formation adjacent seals 101, of a region whose pressure is low, relative to the pressure in medical waste treating chamber 4, which consequently would attract sharp medical waste particles to the seals 101. Low pressure region formation may be prevented by steam being fed along path 111, in a direction leading away from the seals, just prior to steam pressurization of the medical waste treating chamber 4.

In the illustrated embodiment, the path 111 is adjacent to the shaft 17. The path 111, in the illustrated embodiment, includes, proceeding in the direction in which steam is supplied, a first horizontal path segment or conduit segment 112, a first vertical segment 113, a second horizontal segment 115, a second vertical segment 117, a third horizontal segment 119, a third vertical segment 121 (which in the illustrated embodiment comprises a narrow channel between the shaft 17 and a typically bronze sleeve as shown), a fourth horizontal segment 123, an inclined segment 125, and a fifth horizontal conduit segment or path segment 127, however it is appreciated that this is not intended to be limiting. It is appreciated, however, that the path 111, if provided, need not have this particular configuration and may be designed in any suitable manner so as to provide a narrow steam channel preserving the cleanliness of the knife block and preventing malfunction as a result of blockage, as described herein, e.g. by causing a pressure gradient adjacent the seals which distances dirt particles from the seals by providing pressure under the ramp channel or cone 107, as high as or higher than the pressure in waste chamber 4.

Typically, the architecture is such that the only communication path between the debris in the chamber and the seals is via a typically inclined conduit segment 125 typically defined by a ramp structure 107, also termed herein a "cone", such that debris needs to rise along the inclined plane defined by the segment 125 in order to reach the seals 101. Typically, steam is pushed along the conduit 111 which is the only communication path between the debris in the chamber 4 and the seals 101 to further prevent debris from reaching the seals 101. The seals 101 are typically located in an area, e.g. the area below the cone 107, whose pressure is high relative to the pressure in the chamber such that a pressure gradient prevents debris from reaching the seals 101. As shown in FIGS. 7a-7c, the shaft 17 typically has external threading configured and arranged, e.g. relative to the conduit 111 which is the only communication path between the debris in the chamber and the seals, to carry debris away from the seals 101 as the shaft 17 rotates.

As shown in FIG. 6a, the particle ramp 107 typically surrounds the shredder driving shaft 17 and shelters the seals, enabling a high pressure area to be maintained, below the particle ramp, adjacent the seals 101. The high pressure area is typically generated via a steam feeding channel 109.

The path of the steam, which typically reaches the chamber along the inclined path segment 125, is shown by a dotted line 111 in FIG. 4b. Typically, the steam can only reach the chamber via path 111. The steam provided along the path 111 pushes debris away from the seals back to the chamber 4.

The external thread 190 typically provided on the shaft 17 is advantageous in that, when the shaft 17 is rotating so as to drive the shredder blades 18, the thread 190 propels debris if any, out of the vicinity of the seals 101, through the conical ramp. Typically, provision of an inclined exclusive path for the debris as shown, makes it difficult for the debris to elevate, and this feature in combination with the steam pushed into the conduit 111 makes it extremely unlikely for debris to reach and damage the seals 101. A plug 194 (FIG. 4b) is typically provided to prevent leakage of the high pressure steam.

Figure 8:
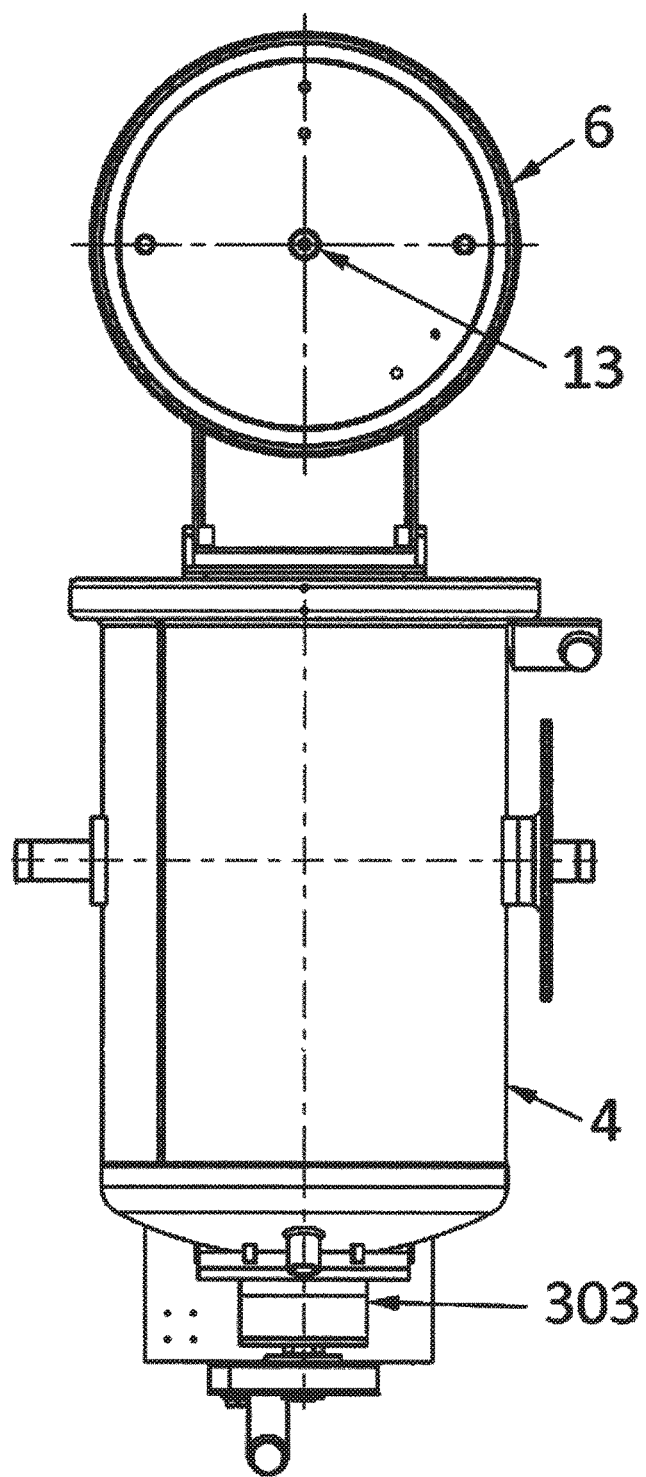
FIG. 8 is a front view of an integrated sterilizer & shredder system in accordance with certain embodiments of the present invention, shown with opened top lid when the assembled vessel, including waste chamber, is in a vertical position, and wherein two side shafts are provided to enable rotating of the waste chamber e.g. between the positions shown in FIGS. 1a-1c, e.g. by means of a chain sprocket.

FIG. 8 is a front view of an ISS system in accordance with certain embodiments of the present invention, shown with opened top lid when the assembled vessel, including waste chamber, is in a vertical position. Typically, as shown, two side shafts are provided to enable rotating of the waste chamber 4 e.g. between the positions shown in FIGS. 1a-1c, e.g. by means of a chain sprocket.

An example Steam Sterilizer with an integrated shredder, intended for treatment of medical waste in hospitals and clinics, is now described in detail with reference to FIGS. 11a-11b, 12a-12c, 13a-13b, 14a-14d and 15.

The system includes an electrically heated bio-hazard sterilizer, which operates with saturated steam as a sterilizing agent, and has a temperature range of up to 138° C. (280.4° F.) and pressure up to 2.4 bars (35 psi). The device includes a large steam sterilizer in accordance with EN285, continuously operated, optionally including only ordinary equipment without applied parts and without signal input-output parts.

The Chamber and the Steam Generator may for example be constructed of stainless steel and the knife of carbon steel. Heating of the waste chamber 4 may be provided by saturated steam supplied by an external steam generator. Metal parts in the inner surfaces are also typically made of stainless steel. The device's chamber is, according to one embodiment, equipped with a single door, provided with an automatic locking mechanism, activated by compressed air, preventing the opening of the door by a safety lock.

The IS S's operating cycles are typically user-specified. Only one general program may be available: Sterilization and shredding 134° C./10 Minutes, bottom (fast) exhaust, 5 minutes drying. In addition, a dynamic test program and a washing 5 cycle are available. The service cycles, e.g. as below, may be protected by code for operation by technical staff only:

Sterilization and shredding 134° C./10 minutes without bottom (fast) exhaust.

Sterilization 134° C./10 minutes without shredding, and without bottom exhaust (fast).

The control system of the device is typically based on state of the art microcomputer technology, ensuring highly reliable and safe operation. The computerized control unit typically ensures fully automatic operation through the entire cycle; hence typically, after setting the pre-selected data and starting the operation, no further intervention is necessary.

The selected program, the phases of the cycle and the status of the machine are typically controlled and displayed on digital readouts.

For optimal control accuracy of the sterilization parameters, the system is equipped with temperature sensors PT100 and three pressure transducers having the following functions:

A temperature sensor for chamber temperature

A temperature sensor for the filter's temperature

A temperature sensor for the drain box's temperature (control and monitoring).

A pressure transducer for chamber pressure

A pressure transducer for generator pressure (control of the generator and monitoring).

A pressure transducer in the over-pressurized sealing area for the knife shaft (safety and monitoring).

The panel located on the front panel typically enables the operator to start and stop the cycle.

The operator starts the machine after putting the waste into the vessel.

An example bio-hazard sterilizer and shredder is now described. It is appreciated that the particular characteristics thereof are not intended to be limiting and any individual parameter or characteristic set out herein may be modified or omitted as suitable.

The ISS processes regulated medical waste into ordinary municipal solid waste. This means that the resultant sterile output can be safely disposed as regular municipal waste. The action of the shredding blades allows steam to penetrate the waste more efficiently and eliminates the possibility of cold spots. The resultant waste is typically unrecognizable and reduced by 50-80%. Post processing, the treated waste is suitable for regular disposal.

As shown in the example piping diagram of FIG. 11*a*, operation may be as follows or any suitable variation or generalization of the following: after loading the chamber, the door automatically closes and the chamber rotates to working position (e.g. fully vertical). At this stage, one vacuum pulse of up to 35 kPa is implemented through valve no. 9, through the bio filter. After vacuum is created, steam is introduced through a lower steam filter (valve no. 3 in FIG. 11*a*), until sterilization temperature is achieved. The shredder blades start rotating from the moment of cycle starting.

During inflation of the chamber with steam, the bio filter valve (6) is opened, until the steam replaces the air completely. This valve releases air through the bio-filter to the drain box. The drain box includes a float switch and a temperature sensor, to verify that no blockage has occurred, and to control the temperature of water going to the drain. In case of blockage, the exhaust is stopped and a failure indication will be provided. During sterilization, the bio filter functions as an integral part of the chamber being sterilized.

Compressed air is introduced through valve no. 4 (Clean filter) to clean the filter.

As described above, the vessel or chamber is equipped with a multipurpose shredder/crusher blade typically on the bottom, to ensure use of the full volume of the vessel. It is regulated by an electric motor which drives the knife shaft through a tooth belt. The shaft connects the knife to the motor through the bearing housing and the sealing area. The motor is of 5.5 kW and is sufficient to rotate the shaft with an RPM of, say, 300-1400 which, according to certain embodiments, depends on the operations being performed. For example, (a first and higher rotational speed, e.g. of 1330 rpm, may be provided for fast and fine shredding useful in order to eliminate large particles, whereas a second, lower rotational speed, e.g. of 300 rpm, may be provided for slow shredding and moving of particles to allow the steam to penetrate throughout the waste. The blades are mounted on the shaft and are typically designed to shred waste such as paper, textiles, plastic and glass. The blade is typically made of high carbon steel with hardened cutting edges.

Utility connections may include an electricity connection, a mineral free water connection, an external steam connection, a water inlet, a drain outlet and a compressed air inlet. For example: Electrical: 400V 3-ph, 16 or 25 kW; External Steam: 30 KG/hr. at 6 bar; 30 l/min. cold water, ½" connection; Drain: 2"-4"; Compressed Air: 6 bar; HVAC: Standard computer environment, 10 air exchanges/hour in room, machine connection to outside vent. The mineral-free water supplied to the steam generator, including steam supplied from boilers installed at the customer's site, which enters the sterilizer chamber, may have the physical characteristics and maximum acceptable level of contaminants indicated in the "Maximum values of contaminants in Feed water and Condensate" table of FIG. 14*b*.

Figure 11B:
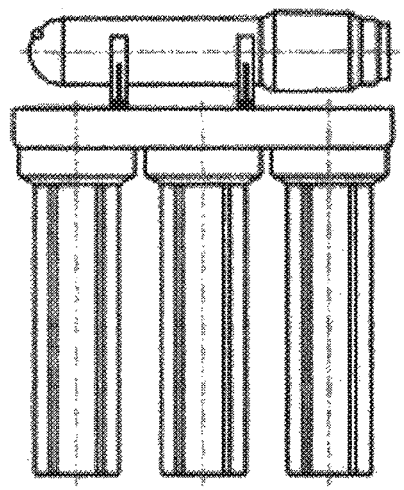

A reverse osmosis water purification system, e.g. as shown in FIG. 11*b*, is provided according to certain embodiments, in order to improve the quality of the water used to generate steam into the device's chamber. The use of mineral-free water contributes to better performance and longer life of the sterilizers' pipes and valves.

The reverse-osmosis water purification system typically obviates any need to refill water reservoirs.

A dynamic test is typically performed at intervals, e.g. at least once every working week, to detect leaks which under pressure may cause infection to the operator and the environment. Operations sequence of this test may include some or all of the following steps, suitably ordered e.g. as shown:

Water and steam are introduced into the empty chamber at 138° C. for a preset pressure (2.4 bar), for 5 min.

The shredder is operated to create a vortex.

During periodic maintenance, or if a leak has been detected during this test, leak detection foam may be used to detect the source of leakages during this test.

A suitable cleaning cycle operations sequence may include some or all of the following steps, suitably ordered e.g. as shown:

Water and steam are introduced into the empty chamber for 5 min; steam is introduced to the filter to clean any remaining residues.

The system holds a temperature of 60° C. in the chamber for 2 minutes, while the shredder works at high speed.

Pressurizing the chamber to 150 kPa with steam and compressed air.

Drainage of the water and residue into the drain box via the fast exhaust valve.

Adding Water for 2 minutes. The shredder's motor is stopped.

Pressurizing the chamber to 110 kPa with steam and compressed air.

Drainage of the water into the drain box via the fast exhaust valve.

FIG. 11a is a piping diagram of a shredder of an example ISS system constructed and operative in accordance with an embodiment of the present invention. The various components of the apparatus of FIG. 11a may, for example, be as indicated in the table of FIGS. 11c-11d.

Figure 12A:
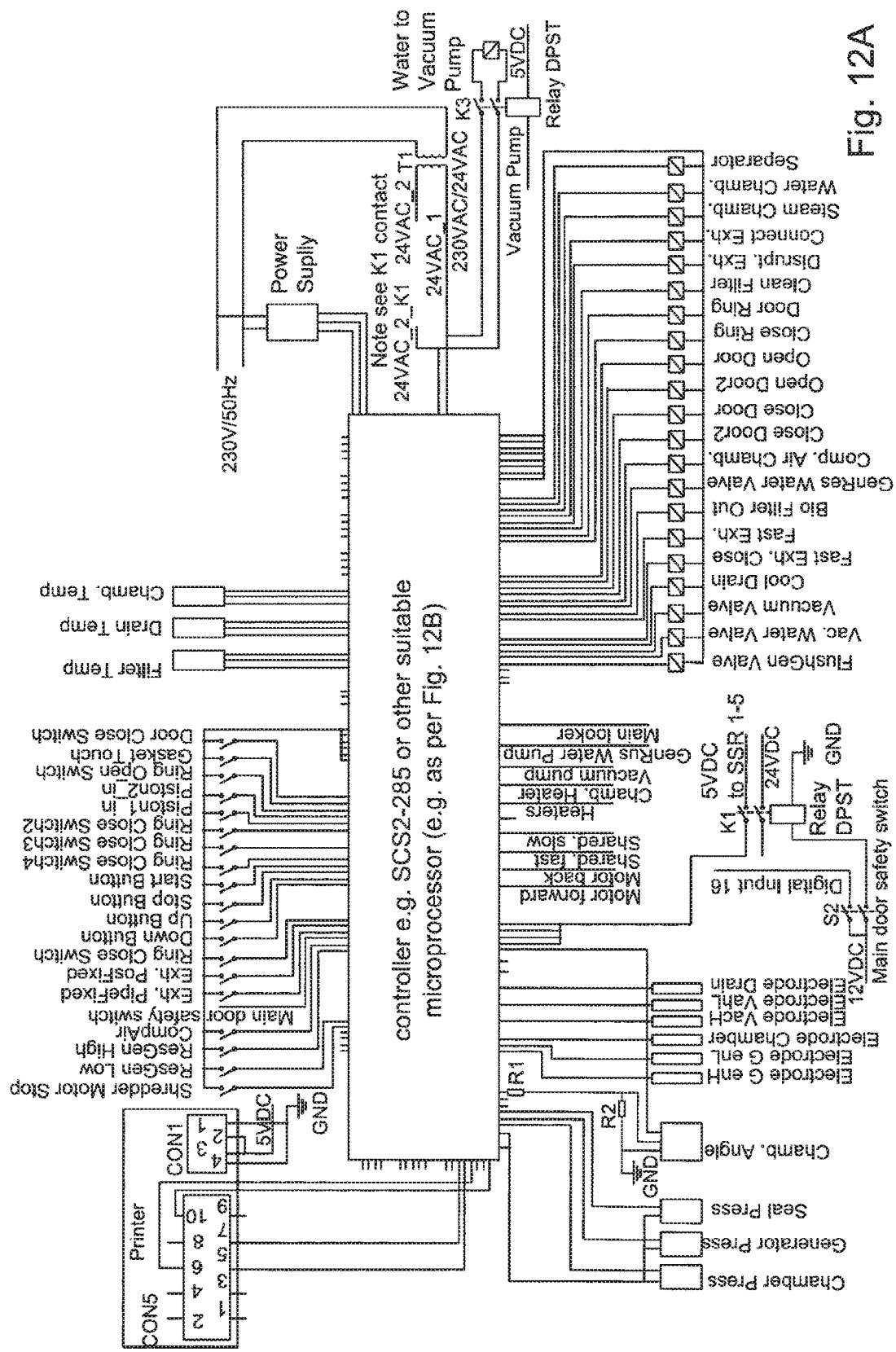
Figure 12B:
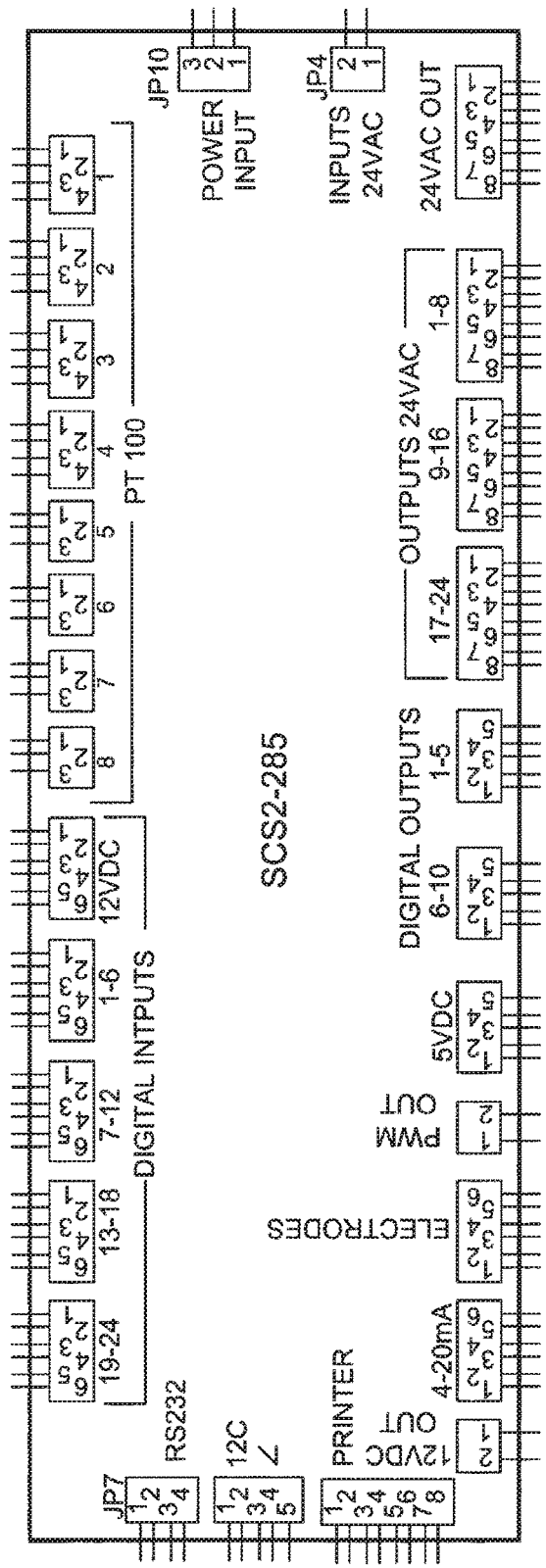
Figure 13A:
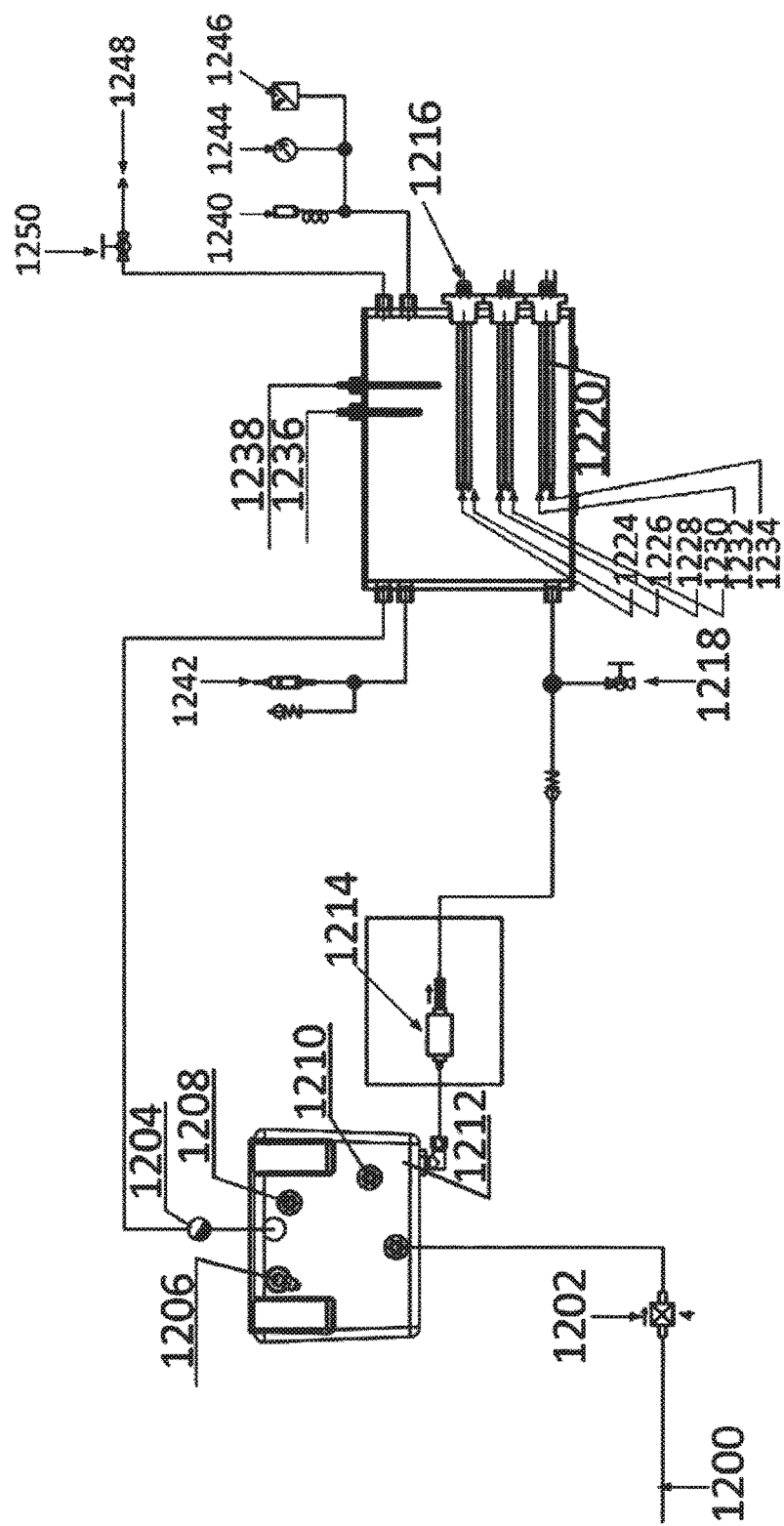

FIG. 12a is an electrical schematic diagram of the control part of an example ISS system constructed and operative in accordance with an embodiment of the present invention. The controller may for example comprise a SCS2-285 or any other suitable microprocessor (e.g. as per FIG. 12b). It is appreciated that FIG. 12a is merely an example of an overview of a possible control system with all inputs and outputs connected to the control system, as well as a main power supply. FIG. 12b is a zoom-in diagram of an example controller suitable for implementing the embodiment of FIG. 12a.

Figure 12D:
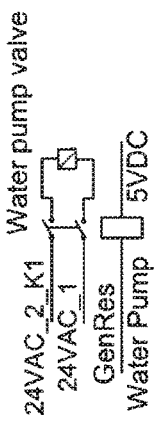
Figure 12C:
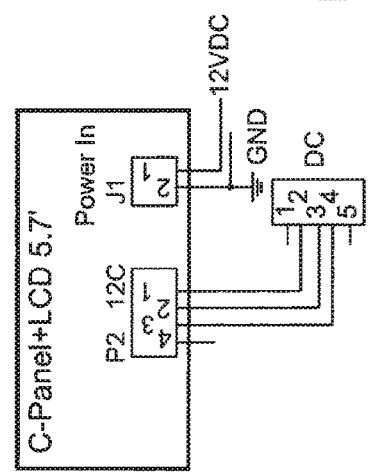

FIGS. 12c and 12d are schematic diagrams of components useful in conjunction with the apparatus of FIG. 12a; in particular, FIG. 12C illustrates a "CPanel" including GUI operator panel with power supply and connection to the control system of FIG. 12b, e.g., through the communication connector marked "12c" in FIG. 12B, left side, under RS232 connector. FIG. 12D illustrates a water pump valve which may be connected to a 24 VAC power and to the control system.

FIG. 13a is a piping diagram of a steam generator of an example ISS system constructed and operative in accordance with an embodiment of the present invention. The various components of the apparatus of FIG. 13a may, for example, be as indicated in the table of FIG. 13c.

Figure 13B:
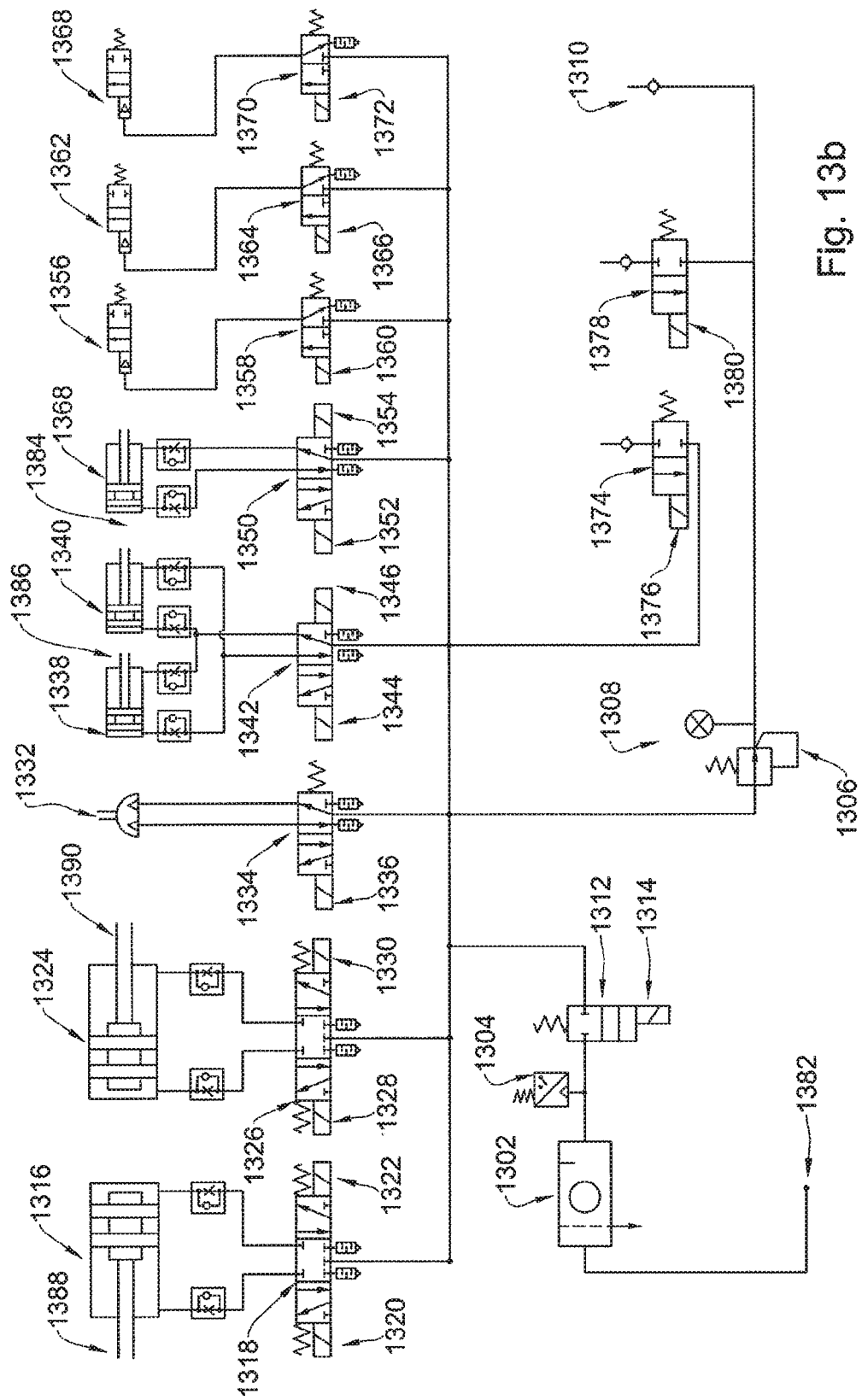

FIG. 13b is a pneumatic diagram of an example ISS system constructed and operative in accordance with an embodiment of the present invention. The various components of the apparatus of FIG. 13b may, for example, be as indicated in the table of FIGS. 13d-13e.

FIG. 14a is a table of specifications for an example ISS system constructed and operative in accordance with an embodiment of the present invention.

FIG. 14b is a table of maximum contaminant values for an example ISS system constructed and operative in accordance with an embodiment of the present invention.

FIG. 14c is a table of valve numbering, which is useful in understanding the piping diagram of FIG. 11a.

FIG. 14d is a table of commercially available products which are examples of possible implementations of certain components of certain embodiments of the present invention, as indicated.

FIG. 14e is a table of commercially available pressure sensors which are examples of possible implementations of certain pressure sensing components of certain embodiments of the present invention, as indicated.

Figure 16:
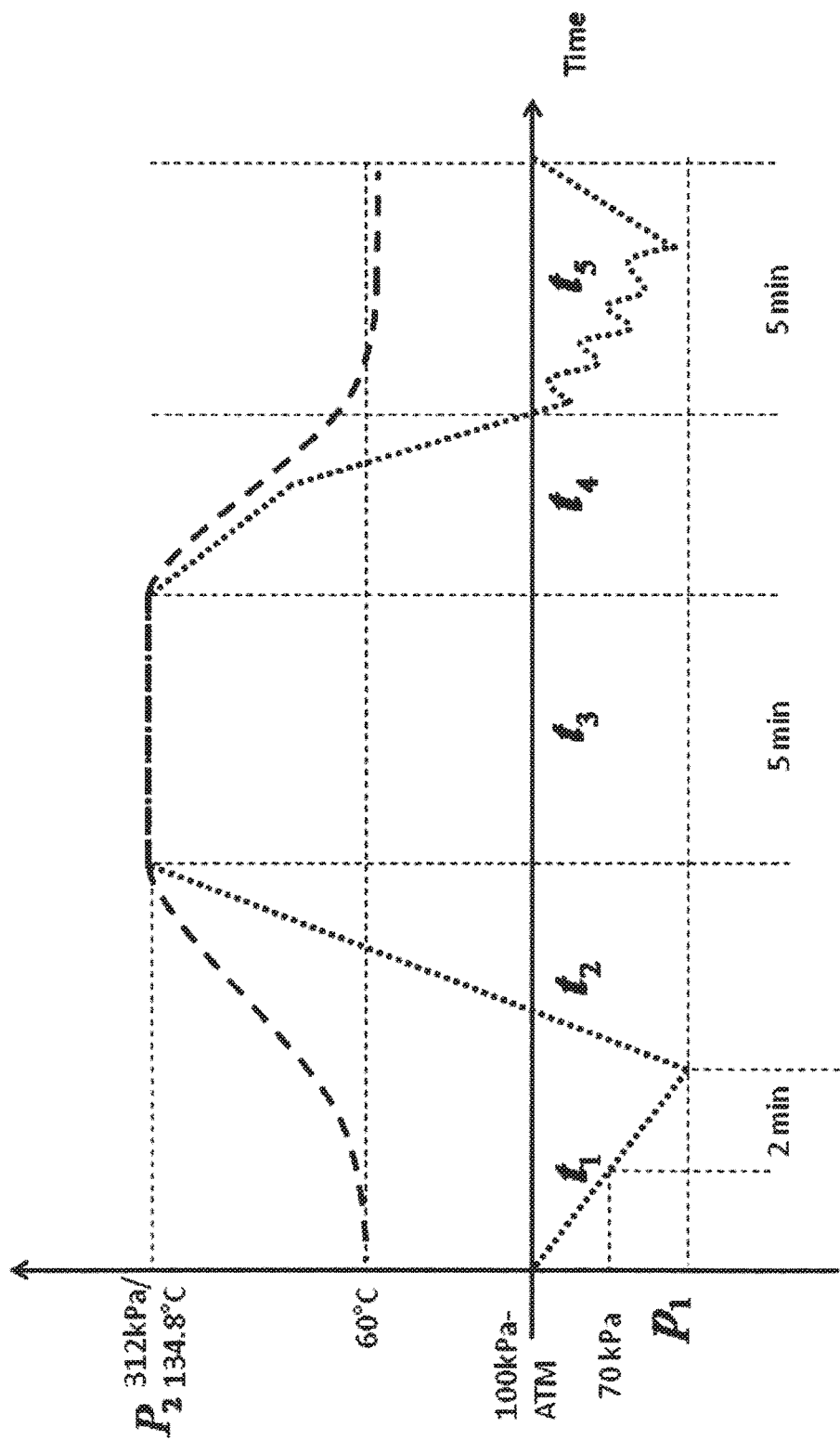
FIG. 16 is a graph of pressure (dotted line) and temperature (dashed line) vs. time, useful in understanding certain embodiments of the present invention.

FIG. 16 is a graph of pressure (dotted line) and temperature (dashed line) vs. time. t1-t5 are time windows, not necessarily to scale, devoted respectively to Pre-vacuum, Heating to Sterilization Temperature (Ster. Temp), Sterilization, Exhaust and Dry functionalities.

Figure 17:
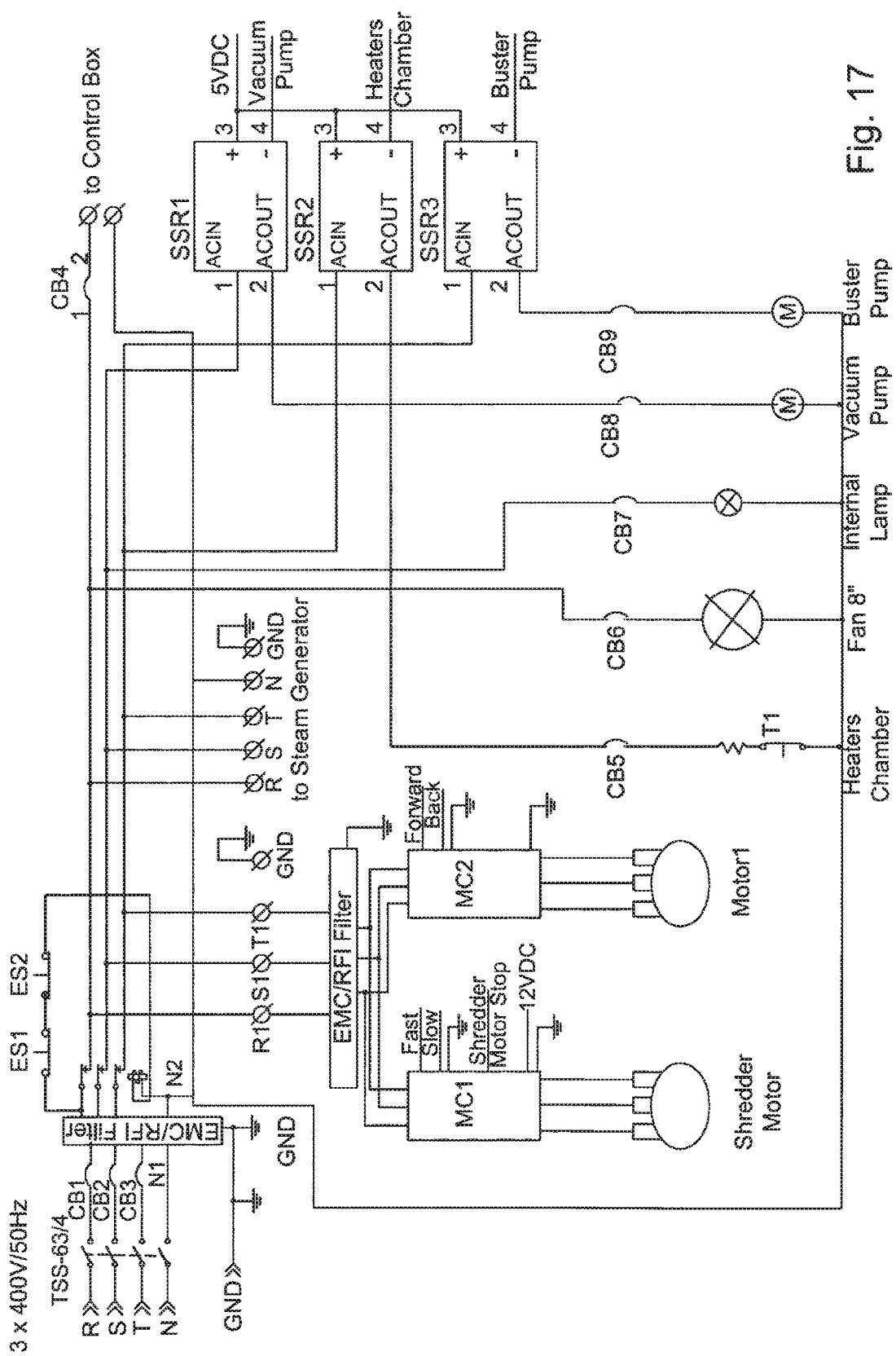

FIG. 17 is an electrical schematic diagram of an example control for the AC portion of an example ISS system constructed and operative in accordance with an embodiment of the present invention.

Figure 18:
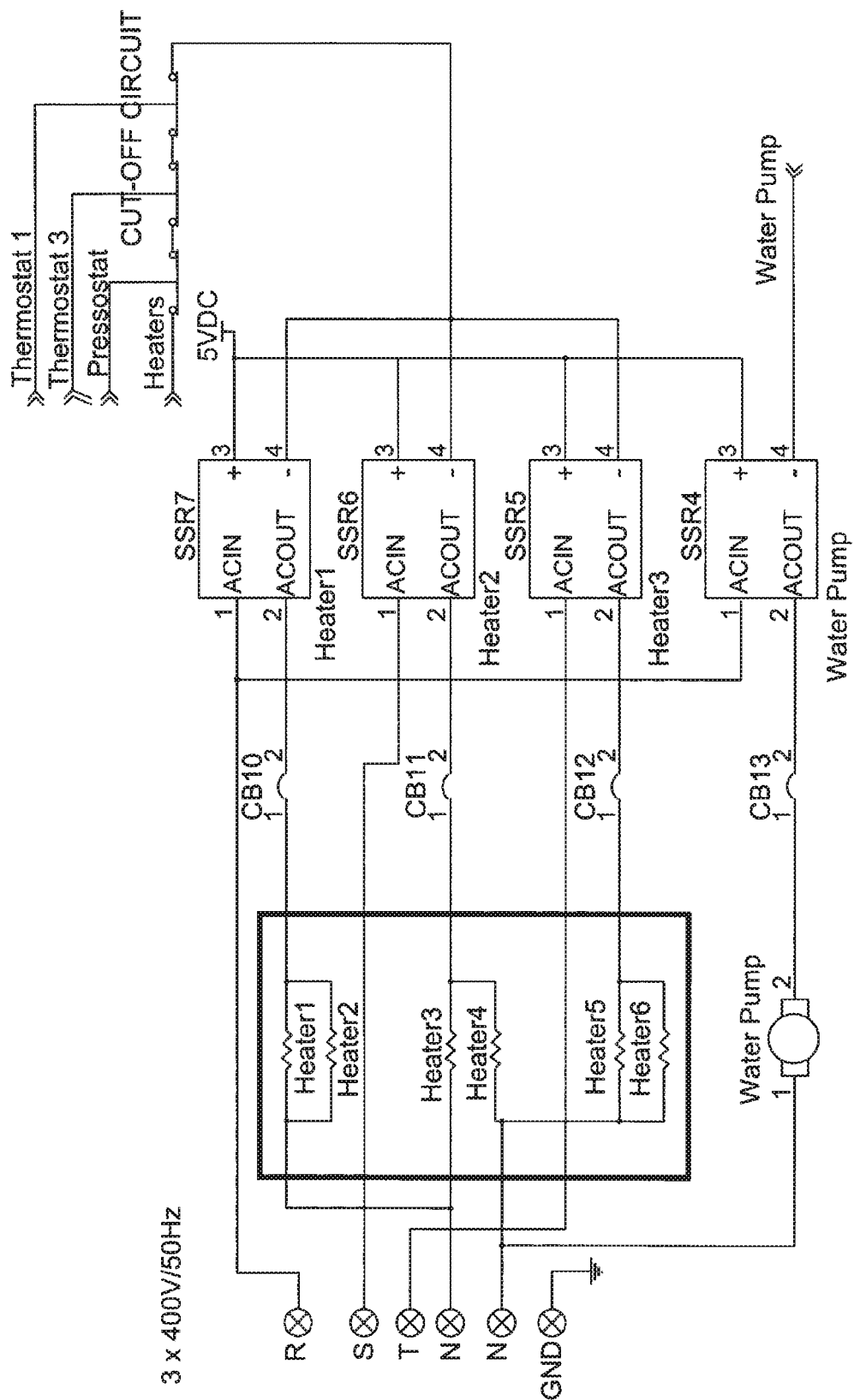

FIG. 18 is an electrical schematic diagram of an example control for the steam generator part of an example ISS system constructed and operative in accordance with an embodiment of the present invention.

The system typically allows changing parameters of the selected program. Options provided may include some or all of: Change Parameters, Analog Inputs, Digital I/O, Calibration, Manual Mode, Maintenance, and Screen Contrast.

Programmable Cycle Parameters may include some or all of:

| | |
|---|---|
| Ster Temp | 134.0 |
| Ster Time | 005.0 |
| Dry Time | 005.0 |
| Vac Pulses | 0001 |
| End Temp | 090.0 |
| SterPressAdd | 012.0 |
| ATMPressure | 100.0 |
| Pulse Vac1 | 070.0 |
| Pulse VacTI | 0120 |
| Pulse Press1 | 050.0 |
| Pulse Vac2 | 030.0 |
| Pulse Vac T2 | 0025 |
| Pulse Press2 | 090.0 |
| Pulse Vac3 | 030.0 |
| Pulse Vac T3 | 0025 |
| Pulse Press3 | 050.0 |

(in the above list, example values are shown).

Analog Inputs may include some or all of:

| | |
|---|---|
| ChambPress | 100.0 |
| Gen Press | 308.2 |
| Seal Press | 380.1 |
| ElectrVacH | 400.0 |
| ElectrVacL | 400.0 |
| ElectDrain | 400.0 |
| CHamb.Angle | 365.9 |
| Chamb Temp | 025.0 |
| Drain Temp | 025.0 |
| ElectrGenH | 400.0 |
| ElectrGenL | 400.0 |
| Press 3 | 100.0 |
| Press 10 | 100.0 |
| ElectrChamb | 400.0 |
| Temp 8 | 025.0 |

(in the above list, example values are shown).

Digital inputs may for example include some or all of:
DoorCLosesSw
Gasket Touch
RingOpenSw
Piston2_In Piston1_In
RingCloseSw2
RingCLoseSw3
RingCloseSw4
StartButton
StopButton
Up Button
Down Button
RingCloseSw
Exh.PosFixed
ExhPipeFixed
SafetyMainSw
Digital outputs may for example include some or all of:
Heaters
Chamb.Heater
Vacuum Pump
Water Pump
Main Locker
Motor Forward
Motor Back
Shred.Fast
Shred.Slow
DigOut5v09
Separator
Water.Chamb.
Steam.Chamb.
Connect Exh
Disrupt Exh
Clean Filter Calibration of analog inputs may be provided. In this case, typically, an 'ANALOG INPUTS' screen is provided on which the names and real-time values of all-analog inputs which the system has are displayed. Also, a 'CALIBRATION' screen is provided which may display chamber pressure and provide user input options such as but not limited to: Change GainOffset, Compute GainOffset and Restore Values. Compute Gain & Offset, for ChambPress 101.0, may for example yield the following:
AH: 300.0 RH: 300.0 AL: 100.0 RL: 100.0

The displayed lists may be browsed to select values to be calibrated.
Available Calibration Operations may include:
Change Gain & Offset—Direct typing of Gain and Offset values.
Compute Gain & Offset—Computing Gain and Offset by two points.
Restore Values—Restore Gain and Offset values with factory defaults.

Typically, computation of calibration values for the analog inputs (temperature, pressure) is performed digitally way and not by adjustment of trimmer pots (potentiometers). The temperature and pressure measuring circuits are typically designed with components having a 1% precision. The temperature circuit is typically linear and has an output of 100 mV÷2400 mV for a temperature range 20÷150° C. The pressure circuit is also linear and has an output of 100 mV÷2400 for a pressure range 0 to 400 kPa. The measuring at the A/D is void for values higher than 2400 mV or lower than 100 mV.

Even though the precision of the components of the circuit is 1%, the accumulated error might reach ±5%, therefore calibration is typically provided. The system is provided with non-erasable memory in which the offset and gain data of the sensors are stored. This data may be fed to the system through programming or through the machine.

Calibration of temperature and pressure through the machine is now described. Programming calibration procedure may be generally the same. The machine is based on the computation of offset and gain from two points.

Figure 15:
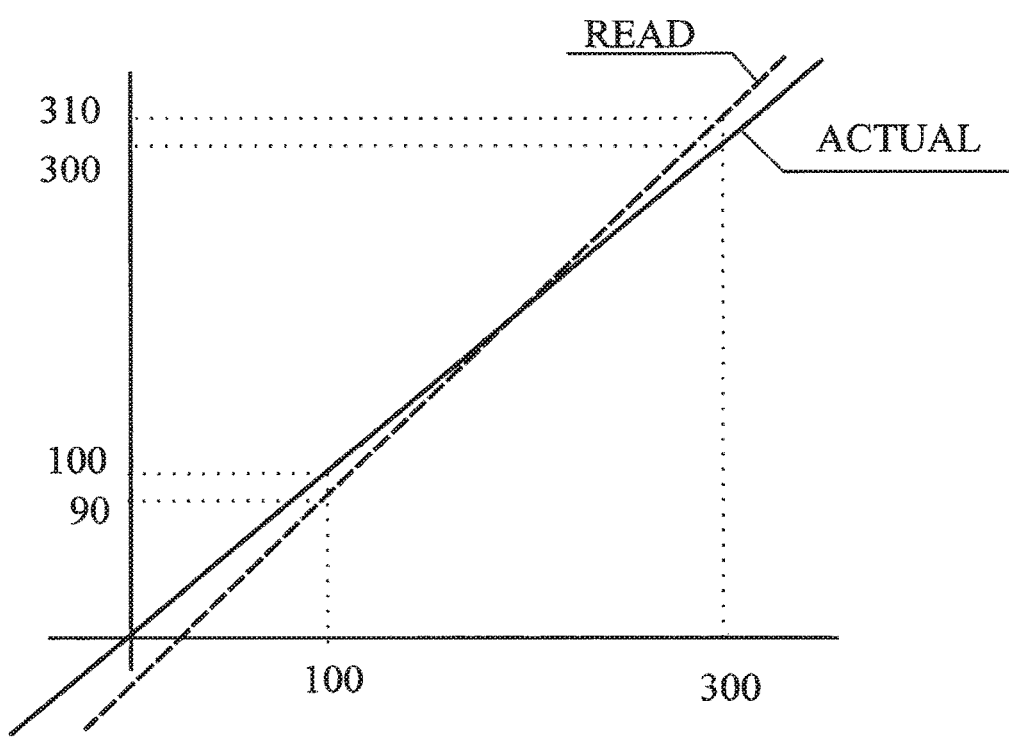

FIG. 15, for example, is a graph of the actual and measured values which may result if the actual pressure is 100 kPa and the system measures and displays 90 kPa and if the actual pressure is 300 kPa and the system measures and displays 310 kPa. The calibration method enables these data to be introduced into the system in order to perform automatic correction of the OFFSET and GAIN. The method may include:
1. Browse the calibration list using the UP and DOWN keys and select the required:
a. Read.H:—Read high value of the analog input.
b. Act. H:—Actual high value of the analog input.
c. Read.L:—Read low value of the analog input.
d. Act. L:—Actual low value of the analog input.

Typically, a GUI enables to view system's I/O, including analog inputs, digital inputs and digital outputs e.g. as described above. Suitable stage messages may be provided. For example, exhaust stage messages may include the following:
Exh Water Cooling, signifying Cooling of the chamber through the water sprinkler.
Exh Pressurizing, signifying pressurizing the chamber with compressed air before water removal.
Exh Water Remove, signifying removing water from the chamber.
Exh Finalizing, signifying that the machine is waiting for the safety pressure and temperature in the chamber.
Other status messages, some or all of which may be displayed in order to monitor the device's status and cycle progress include:
Ready: This message is displayed during the standby stage when the device is ready to start a new cycle.
FAIL: This message is displayed during the standby stage when sterilization cycle fails.
Door Open: This message is displayed during the standby stage when the door is open.
Opening Door: This message is displayed during the standby stage when the door is on unlocking process.
Water Inlet: This message is displayed during the process when the water inlets to the chamber.
Steam On: This message is displayed during the heating stage when the system creates pressure by steam in the chamber.
Heating to Ster.: This message is displayed during the heating stage when the system creates sterilization conditions.
Sterilizing: This message is displayed during the sterilization stage.
Exhaust: This message is displayed during the exhaust stage.
Dry: This message is displayed during the dry stage.
CYCLE END: This message is displayed during the standby stage when the sterilization cycle successfully ends.
TEST ENDED: The message is displayed when the dynamic test is finished.
Recommendations for waste segregation include working separately on non-infectious waste, infectious waste, highly non-infectious waste, and sharp particle waste.
The sterilizer is equipped with two safety valves, located at the chamber and the steam generator.
The valves in FIG. 11a are numbered according to its function, as indicated in the table of FIG. 14c.
It is appreciated that terminology such as "mandatory", "required", "need" and "must" refer to implementation choices made within the context of a particular implementation or application described herewithin for clarity and are not intended to be limiting since in an alternative implantation, the same elements might be defined as not mandatory and not required or might even be eliminated altogether.

It is appreciated that software components of the present invention including programs and data may, if desired, be implemented in ROM (read only memory) form including CD-ROMs, EPROMs and EEPROMs, or may be stored in any other suitable typically non-transitory computer-readable medium such as but not limited to disks of various kinds, cards of various kinds and RAMs. Components described herein as software may, alternatively, be implemented wholly or partly in hardware, if desired, using conventional techniques. Conversely, components described herein as hardware may, alternatively, be implemented wholly or partly in software, if desired, using conventional techniques.

The scope of the present invention is not limited to structures and functions specifically described herein and is also intended to include devices which have the capacity to yield a structure, or perform a function, described herein, such that even though users of the device may not use the capacity, they are if they so desire able to modify the device to obtain the structure or function.

Features of the present invention which are described in the context of separate embodiments may also be provided in combination in a single embodiment. Conversely, features of the invention, including method steps, which are described for brevity in the context of a single embodiment or in a certain order may be provided separately or in any suitable subcombination or in a different order. "e.g." is used herein in the sense of a specific example which is not intended to be limiting. The term "main" and the like as used herein refer to components of the system, some or all of which may be provided according to certain preferred embodiments.

It is appreciated that in the description and drawings shown and described herein, functionalities described or illustrated as systems and sub-units thereof can also be provided as methods and steps therewithin, and functionalities described or illustrated as methods and steps therewithin can also be provided as systems and sub-units thereof. The scale used to illustrate various elements in the drawings is merely exemplary and/or appropriate for clarity of presentation and is not intended to be limiting.

The invention claimed is:

1. A system for shredding and separating liquids from medical waste, the system comprising:
    a medical waste treating chamber;
    a rotating shredder seated in the chamber;
    an apertured partition seated below the rotating shredder and having at least one aperture defined therewithin, thereby to partition the chamber into two compartments communicating only via the at least one aperture; and
    an aperture cleaner below, and fixedly associated with, the rotating shredder and configured and arranged to sweep non-fluids away from said at least one aperture as said rotating shredder rotates;
    the medical waste treating chamber being an interior of an enclosure disposed within an environment;
    the system also comprising:
    at least one high-speed seal to seal off said interior from the environment; and
    a steam generator operative to generate steam in the chamber by pressuring a region adjacent the at least one high-speed seal so as to deter sharp particles within the medical waste, from approaching the at least one high-speed seal.

2. The system according to claim 1 wherein said chamber is cylindrical and has an axis and wherein said aperture cleaner comprises at least one cleaning rod which is disposed at a radial distance relative to the axis and which extends from said rotating shredder downward toward said apertured partition and wherein said at least one aperture comprises a plurality of apertures and wherein said apertured partition comprises a horizontal plate defining a centered circular track of radius r along which said plurality of apertures are defined and along which the at least one cleaning rod travels when the rotating shredder is rotating, thereby to sweep non-fluids away from said plurality of apertures.

3. The system according to claim 1 and also comprising at least one internal liquid sprinkler using sprinkled liquid to provide automatic cleaning of said medical waste treating chamber and wherein said sprinkled liquid travels through said at least one aperture.

4. The system according to claim 1 wherein said aperture partition has top and bottom surfaces and said at least one aperture defines a first hole in said top surface and a second hole, in said bottom surface, which is larger than said first hole, thereby to prevent particles from blocking the at least one aperture.

5. The system according to claim 1,
    the rotating shredder including a motor-driven shaft and blades rotated by the shaft, the shaft extending through the enclosure thereby to define an interface between the waste treating chamber and the environment,
    the system also comprising interface seal apparatus preventing leakage of at least fluids from said medical waste treating chamber into the environment, via the interface,
    thereby to prevent pollution of an environment within which the enclosure is disposed.

6. The system according to claim 5 wherein the medical waste treating chamber is cylindrical and has a bottom portion and wherein said rotating shredder is seated in the bottom portion of the medical waste treating chamber, and wherein the motor is external to the medical waste treating chamber and wherein said interface is cylindrical.

7. The system according to claim 5, the system comprising:
    an apertured partition seated below the rotating shredder and having at least one aperture defined therewithin, thereby to partition the chamber into two compartments communicating only via the at least one aperture; and
    an aperture cleaner below, and fixedly associated with, the rotating shredder, configured and arranged to sweep non-fluids away from said at least one aperture as said rotating shredder rotates.

8. The system according to claim 5 and also comprising a steam sterilizer operative to steam-sterilize contents of the medical waste treating chamber.

9. The system according to claim 1, the system also comprising:
    a vacuum pump operative to eliminate air pockets in the medical waste treating chamber.

10. The system according to claim 1 and also comprising a steam delivering conduit leading from the steam generator to an area adjacent the at least one high-speed seal thereby to prevent formation adjacent the at least one high-speed seal, of a region whose pressure is low, relative to the medical waste treating chamber pressure, which consequently would attract sharp medical waste particles to the at least one high-speed seal, low pressure region formation being prevented by steam pressurizing the area adjacent the at least one high-speed seal just prior to steam pressurization of the medical waste treating chamber.

11. A method for shredding and separating liquids from medical waste, the system comprising:
   providing a rotating shredder seated in a medical waste treating chamber and an apertured partition seated below the rotating shredder and having at least one aperture defined therewithin, thereby to partition the chamber into upper and lower compartments communicating only via the at least one aperture; and
   providing an aperture cleaner below, and fixedly associated with, the rotating shredder and configured and arranged to sweep non-fluids away from said at least one aperture as said rotating shredder rotates;
   the medical waste treating chamber being an interior of an enclosure disposed within an environment;
   the method also comprising:
      providing at least one high-speed seal to seal off said interior from the environment; and
      providing a steam generator operative to generate steam in the chamber by pressuring a region adjacent the at least one high-speed seal so as to deter sharp particles within the medical waste, from approaching the at least one high-speed seal.

12. The method according to claim 11 and also including washing said chamber with a fluid which flows into the lower compartment thereby to allow selective removal of the fluid but not of non-fluid waste, from the chamber, via the lower compartment.

13. The method according to claim 11 and also including flushing a fluid through medical waste in the chamber to eliminate malodor, wherein the fluid flows into the lower compartment thereby to allow selective removal of the fluid but not of non-fluid waste, from the chamber, via the lower compartment.

14. The method according to claim 11,
   wherein providing the rotating shredder includes providing a motor-driven shaft and blades rotated by the shaft, the shaft extending through the enclosure thereby to define an interface between the waste treating chamber and the environment,
   the method also comprising providing interface seal apparatus operative to prevent leakage of at least fluids from said medical waste treating chamber into the environment, via the interface,
   thereby to prevent pollution of an environment within which the enclosure is disposed.

15. The method according to claim 11, the method also comprising:
   providing a vacuum pump operative to eliminate air pockets in the medical waste treating chamber, and
   wherein the steam generator is operative to generate the steam in the chamber after the air pockets have been eliminated, thereby to ensure steam sterilization of all waste in the chamber.

16. A system for shredding and separating liquids from medical waste, the system comprising:
   a medical waste treating chamber;
   a rotating shredder seated in the chamber; and
   an apertured partition seated below the rotating shredder and having at least one aperture defined therewithin, thereby to partition the chamber into two compartments communicating only via the at least one aperture;
   the medical waste treating chamber being an interior of an enclosure disposed within an environment,
   the system also comprising:
      at least one high-speed seal to seal off said interior from the environment; and
      a steam generator operative to generate steam in the chamber by pressuring a region adjacent the at least one high-speed seal so as to deter sharp particles within the medical waste, from approaching the at least one high-speed seal.

17. The system according to claim 16 wherein said chamber is cylindrical and has an axis and also comprising an aperture cleaner which comprises at least one cleaning rod which is disposed at a radial distance relative to the axis and which extends from said rotating shredder downward toward said apertured partition, and
   wherein said at least one aperture comprises a plurality of apertures and wherein said apertured partition comprises a horizontal plate defining a centered circular track of radius r along which said plurality of apertures are defined and along which the at least one cleaning rod travels when the rotating shredder is rotating, thereby to sweep non-fluids away from said plurality of apertures.

18. The system according to claim 16 and also comprising at least one internal liquid sprinkler using sprinkled liquid to provide automatic cleaning of said medical waste treating chamber and wherein said sprinkled liquid travels through said at least one aperture.

19. The system according to claim 16 wherein said apertured partition has top and bottom surfaces and said at least one aperture defines a first hole in said top surface and a second hole, in said bottom surface, which is larger than said first hole, thereby to prevent particles from blocking the at least one aperture.

20. The system according to claim 16 and also comprising:
   a vacuum pump operative to eliminate air pockets in the medical waste treating chamber, and
   a steam generator operative to generate steam in the chamber after the air pockets have been eliminated, thereby to ensure steam sterilization of all waste in the chamber.

21. The system according to claim 16 wherein said medical waste treating chamber is defined by an enclosure having an opening at its top for introducing medical waste to be treated into said medical waste treating chamber and wherein said system includes a device arranged and operative to up-end the chamber thereby to remove treated medical waste therefrom via said opening.

* * * * *